United States Patent
Kondoh et al.

(10) Patent No.: US 11,078,271 B2
(45) Date of Patent: Aug. 3, 2021

(54) ANTI-CLAUDIN-2 MONOCLONAL ANTIBODY

(71) Applicants: OSAKA UNIVERSITY, Suita (JP); JAPAN AS REPRESENTED BY DIRECTOR GENERAL OF NATIONAL INSTITUTE OF HEALTH SCIENCES, Kawasaki (JP)

(72) Inventors: Masuo Kondoh, Suita (JP); Kiyohito Yagi, Suita (JP); Akihiro Watari, Suita (JP); Masayoshi Fukasawa, Tokyo (JP); Minoru Tada, Kawasaki (JP); Jun Kunisawa, Ibaraki (JP)

(73) Assignee: Osaka University, Osaka (JP)

( * ) Notice: Subject to any disclaimer, the term of this patent is extended or adjusted under 35 U.S.C. 154(b) by 172 days.

(21) Appl. No.: 16/473,413

(22) PCT Filed: Dec. 25, 2017

(86) PCT No.: PCT/JP2017/046389
§ 371 (c)(1),
(2) Date: Jun. 25, 2019

(87) PCT Pub. No.: WO2018/123949
PCT Pub. Date: Jul. 5, 2018

(65) Prior Publication Data
US 2020/0140542 A1    May 7, 2020

(30) Foreign Application Priority Data
Dec. 28, 2016 (JP) .............................. JP2016-256352

(51) Int. Cl.
*C07K 16/18* (2006.01)
*C07K 16/28* (2006.01)
*A61K 39/395* (2006.01)

(52) U.S. Cl.
CPC .......... *C07K 16/28* (2013.01); *C07K 2317/24* (2013.01); *C07K 2317/33* (2013.01);
(Continued)

(58) Field of Classification Search
None
See application file for complete search history.

(56) References Cited

U.S. PATENT DOCUMENTS

| | | |
|---|---|---|
| 2010/0111852 A1 | 5/2010 | Yoshida |
| 2011/0059469 A1 | 3/2011 | Aburatani et al. |
| 2011/0306126 A1 | 12/2011 | Hashimoto et al. |

FOREIGN PATENT DOCUMENTS

| | | |
|---|---|---|
| JP | 2000-32984 A | 2/2000 |
| WO | 2008/072723 A1 | 6/2008 |

(Continued)

OTHER PUBLICATIONS

Zeissig et al., "Changes in expression and distribution of claudin 2,5 and 8 lead to discontinuous tight junctions and barrier dysfunction in active Crohn's disease," Gut, 56: 61-72 (2006).
(Continued)

*Primary Examiner* — Aurora M Fontainhas
(74) *Attorney, Agent, or Firm* — Morgan, Lewis & Bockius LLP

(57) ABSTRACT

An object of the present invention is to provide a monoclonal antibody that recognizes an extracellular region of Claudin-2. A monoclonal antibody that specifically binds to an extracellular region of Claudin-2.

16 Claims, 26 Drawing Sheets
Specification includes a Sequence Listing.

(52) U.S. Cl.
CPC .. *C07K 2317/732* (2013.01); *C07K 2317/734* (2013.01); *C07K 2317/75* (2013.01); *C07K 2317/92* (2013.01)

(56) References Cited

FOREIGN PATENT DOCUMENTS

| WO | 2009/087978 A1 | 7/2009 |
|---|---|---|
| WO | 2010/064454 A1 | 6/2010 |
| WO | 2014/132307 A1 | 9/2014 |
| WO | 2014/132647 A1 | 9/2014 |

OTHER PUBLICATIONS

Kinugasa et al., "Selective Up-regulation of Claudin-1 and Claudin-2 in Colorectal Cancer," Anticancer Research, 27: 3729-3734 (2007).
Al-Sadi et al., "Interleukin-6 Modulation of Intestinal Epithelial Tight Junction Permeability is Mediated by JNK Pathway Activation of Claudin-2 Gene," PLOS One, 9 (3): e85345 (2014).
Krause et al., "Structure and function of claudins," Biochimica et Biophysica Acta, 1778: 631-645 (2007).
Kobayashi, "Antibody Production by DNA Immunization Method," Journal of Bioscience and Bioengineering, 86 (8): 384-386 (2008) (see partial translation).
Gunzel et al., "Claudins and Other Tight Junction Proteins," Comprehensive Physiology, (2): 1819-1852 (2012).
Furuse et al., "Conversion of Zonulae Occludentes from Tight to Leaky Strand Type by Introducing Claudin-2 into Madin-Darby Canine Kidney I Cells," The Journal of Cell Biology, 153 (2): 263-272 (2001).
Furuse et al., "Claudin-1 and -2: Novel Integral Membrane Proteins Localizing at Tight Junctions with No Sequence Similarity to Occludin," The Journal of Cell Biology, 141 (7): 1539-1550 (1998).
Weber et al., "Claudin-1 and claudin-2 expression is elevated in inflammatory bowel disease and may contribute to early neoplastic transformation," Laboratory Investigation, 88: 1110-1120 (2008).
Virman et al., "Claudins as Prognostic Factors for Renal Cell Cancer," Anticancer Research, 34: 4181-4187 (2014).
Ding et al., "The claudin family of proteins in human malignancy: a clinical perspective," Cancer Management and Research, 5: 367-375 (2013).
Suzuki et al., "Therapeutic antitumor efficacy of monclonal antibody against Claudin-4 for pancreatic and ovarian cancers," Cancer Science, 100 (9): 1623-1630 (2009).
Fofana et al., "Basic-Liver, Pancreas, and Biliary Tract: Monoclonal Anti-Claudin 1 Antibodies Prevent Hepatitis C Virus Inefection of Primary Human Hepatocytes," Gastroenterology, 139 (3): 953-964 (2010).
Li et al., "Development of Anti-Claudin-3 and -4 Bispecific Monoclonal Antibody for Cancer Diagnosis and Therapy," The Journal of Pharmacology and Experimental Therapeutics, 351: 206-213 (2014).
Takahashi et al., "Creation and biochemical analysis of a broad-specific claudin binder," Biomaterials, 33: 3464-3474 (2012).
International Search Report issued in corresponding International Patent Application No. PCT/JP2017/046389 dated Feb. 27, 2018.
Tabaries et al., "Claudin-2 Promotes Breast Cancer Liver Metastasis by Facilitating Tumor Cell Interactions with Hepatocytes," Molecular and Cellular Biology, 32 (15): 2979-2991 (2012).
Kwon, "Emerging Roles of Claudins in Human Cancer," International Journal of Molecular Sciences, 14 (9): 18148-18180 (2013).
Liu et al., "DNA immunization as a technology platform for monoclonal antibody induction," Emerging Microbes & Infections, 5 (1): pp. 1-6 (2016).
Tan et al., "A novel microfluidics-based method for probing weak protein-protein interactions," Lab Chip, 12 (15): 2726-2735 (2012).
Amasheh et al., "Claudin-2 expression induces cation-selective channels in tight junctions of epithelial cells," Journal of Cell Science, 115 (24): 4969-4976 (2002).
Tabaries et al., "Claudin-2 is selectively enriched in and promotes the formation of breast cancer liver metastases through engagement of integrin complexes," Oncogene, 30 (11): 1318-1328 (2010).
Tabaries et al., "Lyn modulates Claudin-2 expression and is a therapeutic target for breast cancer liver metastasis," Oncotarget, 6 (11): 9476-9487 (2015).
Soini, "Expression of claudins 1, 2, 3, 4, 5 and 7 in various types of tumours," Histopathology, 46 (5): 551-560 (2005).
Extended European Search Report issued in corresponding European Patent Application No. 17889515.7 dated Jul. 10, 2020.

A. Xi-1A2

B. Xi-2G8

A

B

A

Data are presented as means ± SD (n=3)
**: p<0.01 vs. Medium

B

Data are presented as means ± SD (n=3)

*: $p < 0.05$ vs. Medium

Data are presented as means ± SD (n=3)

**: p<0.01 vs. 0h

Data are presented as means ± SD (n=3)

**: $p<0.01$ vs. 0μg/mL

A

B

Data are presented as means ± SD (n=3)

A

B

Data are presented as means ± SD (n=3)

Data are presented as means ± SD (n=3)

**: $p < 0.01$ vs. 0μg/mL

Data are presented as means ± SEM (n=4)

∗ : p < 0.05 vs. control rat IgG

Non-transfer

Non-transfer

Transfer control IgG

Transfer control IgG

Transfer 1A2

Transfer 1A2

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: VH CDR1 OF CLONE 1A2

<400> SEQUENCE: 1

His Asp Ile Ile His
1               5

<210> SEQ ID NO 2
<211> LENGTH: 5
<212> TYPE: PRT
```

```
<213> ORGANISM: Artificial Sequence
<220> FEATURE:
<223> OTHER INFORMATION: VH CDR1 OF CLONE 2G8

<400> SEQUENCE: 2

Val Ser Phe Leu His
1               5

<210> SEQ ID NO 3
<211> LENGTH: 14
<212> TYPE: PRT
<213> ORGANISM: Artificial Sequence
<220> FEATURE:
<223> OTHER INFORMATION: VH CDR2 OF CLONE 1A2

<400> SEQUENCE: 3

Tyr Ile Asn Pro Tyr Asn Gly Gly Thr Asn Tyr Asn Glu Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: VH CDR2 OF CLONE 2G8

<400> SEQUENCE: 4

Tyr Ile Asn Pro Tyr Ser Gly Ser Pro Asn Tyr Asn Glu Lys
1               5                   10

<210> SEQ ID NO 5
<211> LENGTH: 5
<212> TYPE: PRT
<213> ORGANISM: Artificial Sequence
<220> FEATURE:
<223> OTHER INFORMATION: VH CDR3 OF CLONE 1A2

<400> SEQUENCE: 5

Gly Ser Phe Asp Tyr
1               5

<210> SEQ ID NO 6
<211> LENGTH: 4
<212> TYPE: PRT
<213> ORGANISM: Artificial Sequence
<220> FEATURE:
<223> OTHER INFORMATION: VH CDR3 OF CLONE 2G8

<400> SEQUENCE: 6

Asn Trp Asp Tyr
1

<210> SEQ ID NO 7
<211> LENGTH: 16
<212> TYPE: PRT
<213> ORGANISM: Artificial Sequence
<220> FEATURE:
<223> OTHER INFORMATION: VL CDR1 OF CLONE 1A2

<400> SEQUENCE: 7

Lys Ser Ser Gln Ser Leu Leu Gly Thr Ser Gly Lys Thr Phe Leu Asn
1               5                   10                  15

<210> SEQ ID NO 8
<211> LENGTH: 16
<212> TYPE: PRT
<213> ORGANISM: Artificial Sequence
```

```
<220> FEATURE:
<223> OTHER INFORMATION: VL CDR1 OF CLONE 2G8

<400> SEQUENCE: 8

Lys Ser Ser Gln Ser Leu Leu Gly Ser Ser Gly Lys Thr Phe Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: VL CDR2 OF CLONE 1A2

<400> SEQUENCE: 9

Gln Val Ser Lys Leu Tyr Ser
1               5

<210> SEQ ID NO 10
<211> LENGTH: 7
<212> TYPE: PRT
<213> ORGANISM: Artificial Sequence
<220> FEATURE:
<223> OTHER INFORMATION: VL CDR2 OF CLONE 2G8

<400> SEQUENCE: 10

Gln Val Ser Thr Leu Tyr Ser
1               5

<210> SEQ ID NO 11
<211> LENGTH: 9
<212> TYPE: PRT
<213> ORGANISM: Artificial Sequence
<220> FEATURE:
<223> OTHER INFORMATION: VL CDR3 OF CLONE 1A2

<400> SEQUENCE: 11

Trp Gln Gly Ile His Phe Pro His Thr
1               5

<210> SEQ ID NO 12
<211> LENGTH: 9
<212> TYPE: PRT
<213> ORGANISM: Artificial Sequence
<220> FEATURE:
<223> OTHER INFORMATION: VL CDR3 OF CLONE 2G8

<400> SEQUENCE: 12

Trp Gln Gly Ile His Phe Pro His Thr
1               5

<210> SEQ ID NO 13
<211> LENGTH: 116
<212> TYPE: PRT
<213> ORGANISM: Artificial Sequence
<220> FEATURE:
<223> OTHER INFORMATION: VH OF CLONE 1A2

<400> SEQUENCE: 13

Gln Val Lys Leu Leu Gln Ser Gly Ala Ala Leu Val Pro Lys Pro Gly
1               5                   10                  15

Asp Ser Met Lys Met Ser Cys Lys Ala Ser Gly Tyr Thr Phe Thr His
                20                  25                  30

Asp Ile Ile His Trp Val Arg Gln Ser His Gly Lys Ser Leu Glu Trp
            35                  40                  45
```

Ile Gly Tyr Ile Asn Pro Tyr Asn Gly Gly Thr Asn Tyr Asn Glu Lys
            50                  55                  60

Phe Lys Thr Lys Ala Thr Met Thr Val Asp Lys Pro Ser Ser Thr Ala
 65                  70                  75                  80

Tyr Leu Glu Leu Thr Arg Val Ser Ser Glu Ala Ser Ala Ile Tyr Tyr
                 85                  90                  95

Cys Ala Thr Gly Ser Phe Asp Tyr Trp Gly Gln Gly Val Met Val Thr
                100                 105                 110

Val Ser Ser Ala
            115

<210> SEQ ID NO 14
<211> LENGTH: 113
<212> TYPE: PRT
<213> ORGANISM: Artificial Sequence
<220> FEATURE:
<223> OTHER INFORMATION: VH OF CLONE 2G8

<400> SEQUENCE: 14

Gln Val Asn Leu Leu Gln Ser Gly Ala Ala Leu Val Lys Pro Gly Ala
 1               5                  10                  15

Ser Val Arg Leu Ser Cys Arg Val Ser Gly Tyr Ser Phe Thr Val Ser
                20                  25                  30

Phe Leu His Trp Val Lys Gln Ser His Gly Lys Ser Leu Glu Trp Ile
                35                  40                  45

Gly Tyr Ile Asn Pro Tyr Ser Gly Ser Pro Asn Tyr Asn Glu Lys Phe
            50                  55                  60

Lys Ser Lys Thr Thr Leu Thr Val Asp Lys Ser Thr Ser Thr Ala Tyr
 65                  70                  75                  80

Met Glu Leu Ser Gly Leu Thr Ser Glu Asp Ser Ala Ser Tyr Tyr Cys
                 85                  90                  95

Thr Asn Trp Asp Tyr Trp Gly Gln Gly Val Met Val Thr Val Ser Ser
                100                 105                 110

Ala

<210> SEQ ID NO 15
<211> LENGTH: 113
<212> TYPE: PRT
<213> ORGANISM: Artificial Sequence
<220> FEATURE:
<223> OTHER INFORMATION: VL OF CLONE 1A2

<400> SEQUENCE: 15

Asp Val Val Leu Thr Gln Thr Pro Gly Ser Leu Ser Leu Ala Ile Gly
 1               5                  10                  15

Gln Ser Ala Ser Ile Ser Cys Lys Ser Ser Gln Ser Leu Leu Gly Thr
                20                  25                  30

Ser Gly Lys Thr Phe Leu Asn Trp Ile Leu Gln Arg Pro Gly Gln Ser
                35                  40                  45

Pro Glu Arg Leu Ile Tyr Gln Val Ser Lys Leu Tyr Ser Glu Val Pro
            50                  55                  60

Asp Arg Phe Ser Gly Ser Gly Ser Glu Thr Glu Phe Thr Leu Lys Ile
 65                  70                  75                  80

Ser Arg Val Glu Ala Glu Asp Leu Gly Val Tyr Tyr Cys Trp Gln Gly
                 85                  90                  95

Ile His Phe Pro His Thr Phe Gly Ala Gly Thr Lys Leu Glu Leu Lys
                100                 105                 110

```
<210> SEQ ID NO 16
<211> LENGTH: 113
<212> TYPE: PRT
<213> ORGANISM: Artificial Sequence
<220> FEATURE:
<223> OTHER INFORMATION: VL OF CLONE 2G8

<400> SEQUENCE: 16

Asp Val Val Met Thr Gln Thr Pro Val Ser Leu Ser Leu Ala Ile Gly
1               5                   10                  15

Gln Pro Ala Ser Ile Ser Cys Lys Ser Ser Gln Ser Leu Leu Gly Ser
            20                  25                  30

Ser Gly Lys Thr Phe Leu Asn Trp Ile Leu Gln Arg Pro Gly Gln Ser
        35                  40                  45

Pro Lys Arg Leu Ile Tyr Gln Val Ser Thr Leu Tyr Ser Glu Val Pro
    50                  55                  60

Asp Arg Phe Ser Gly Ser Gly Ser Glu Thr Glu Phe Thr Leu Lys Ile
65                  70                  75                  80

Thr Arg Val Glu Ala Glu Asp Leu Gly Val Tyr Tyr Cys Trp Gln Gly
            85                  90                  95

Ile His Phe Pro His Thr Phe Gly Ala Gly Thr Lys Leu Glu Leu Lys
            100                 105                 110

Arg
```

ANTI-CLAUDIN-2 MONOCLONAL ANTIBODY

SEQUENCE LISTING SUBMISSION VIA EFS-WEB

A computer readable text file, entitled "SequenceListing.txt," created on or about Jun. 25, 2019 with a file size of about 7 kb contains the sequence listing for this application and is hereby incorporated by reference in its entirety.

TECHNICAL FIELD

The present invention relates to an anti-Claudin-2 monoclonal antibody. More specifically, the present invention relates to a monoclonal antibody that specifically binds to an extracellular region of Claudin-2, as well as relating to uses of the antibody (a pharmaceutical composition containing the antibody, a substance delivery carrier for Claudin-expressing cells containing the antibody, and the like).

BACKGROUND ART

Claudin is a tetra-transmembrane protein having a molecular weight of about 23 kDa identified as a tight junction (TJ) constituent protein in 1998. 27 types of Claudin have been discovered so far (Patent Document 1, Non-Patent Document 1).

Among Claudin-2, which is a member of the Claudin family, human Claudin-2 is known to have a total length of 230 amino acid residues, in which the 28th to 78th amino acids correspond to the first loop of the extracellular region and the 144th to 162nd amino acids correspond to the second loop of the extracellular region. As is clear from the fact that the first loop of the extracellular region has 51 amino-acid residues and the second loop of the extracellular region has 19 amino-acid residues, it has been known that the extracellular region of Claudin-2 is generally small.

Further, it has also been known that the amino acid sequences of Claudin-2 have significantly high interspecies homology. For example, between human Claudin-2 and mouse homologous protein (NCBI accession number: NP057884), the homology of the full-length amino acid sequence length is 91.3%, the homology of the amino acid sequence of the first loop of the extracellular region is 96.1%, and the homology of the amino acid sequence of the second loop of the extracellular region is 100%. Further, between human Claudin-2 and rat homologous protein (NCBI accession number: NP001100316), the homology of the full-length amino acid sequence length is 91.7%, the homology of the amino acid sequence of the first loop of the extracellular region is 96.1%, and the homology of the amino acid sequence of the second loop of the extracellular region is 100%.

Further, there are reports of acceleration of the permeability of substances in epithelial cell layers by Claudin-2 (Non-Patent Documents 2 and 3), an increase in Claudin-2 expression in inflammatory bowel diseases (Non-Patent Document 4), and an increase in Claudin-2 expression in kidney cancers, colon cancers, lung cancers, and liver cancers (Non-Patent Documents 5 and 6), etc.; therefore, Claudin-2 has been attracting attention as a target in drug discovery.

Generally, drug discovery of antibody drugs targeting membrane proteins involves the production of antibodies that recognize the extracellular region. However, even though Claudin-2 is one of the first-identified Claudins, as mentioned above, since Claudin-2 has a small extracellular region and high interspecies homology, no antibody that recognizes the extracellular region of Claudin-2 has been present.

CITATION LIST

Patent Documents

Patent Document 1: JP2000-32984A

Non-Patent Documents

Non-Patent Document 1: Compr. Physiol., 2, 1819, 2012
Non-Patent Document 2: J. Cell Biol., 153, 236, 2001
Non-Patent Document 3: J. Cell Biol., 141, 1539, 1998
Non-Patent Document 4: Lab. Invest., 88, 1110, 2008
Non-Patent Document 5: Anticancer Res., 34, 4181, 2014
Non-Patent Document 6: Cancer Manag. Res., 5, 367, 2013

SUMMARY OF INVENTION

Technical Problem

The present invention was made in light of the current circumstances of prior art described above, and an object of the present invention is to provide a monoclonal antibody that recognizes the extracellular region of Claudin-2, as well as a novel use of the antibody.

Solution to Problem

In order to solve the problems, the inventors of the present invention attempted production of hCL-2 antibody by immunizing autoimmune disease mice by using human Claudin-2 (hCL-2)-expressed cells, based on the report of production of hCL-4 antibody by way of administration of human Claudin-4 (hCL-4)-expressed cells to autoimmune disease mice (Cancer Sci., 100, 1623, 2009). However, the inventors did not succeed in the production of hCL-2 antibody.

Further, previously, the inventors succeeded in the production of human Claudin-1 (hCL-1) antibody and human Claudin-4 (hCL-4) antibody by way of DNA immunization method (International Publication WO2014/132307 and International Publication WO2014/132647).

The inventors of the present invention considered the possibility of producing hCL-2 antibody by a DNA immunization method in light of experience in the production of the hCL-1 antibody and hCL-4 antibody described above. However, as described above, considering that the first loop of hCL-2, which is the largest extracellular region, is short, namely 51 amino-acid residues, and that although the amino acid sequence homology of the first loop of hCL-2 with respect to a rodent homologous protein is significantly high, namely, 96.1%, it is relatively low, namely 93.9% and 90.5%, in hCL-1 and hCL-4, respectively, and also considering the fact that, in general, an antibody of an antigen having a high degree of homology with a host protein is difficult to obtain, and the like, the production of hCL-2 antibody by DNA immunization cannot be readily assumed from the results of the productions of hCL-1 antibody and hCL-4 antibody.

Further, according to information materials provided by the trustee company in charge of the DNA immunization method, only 16 out of 28 examples of antibody production were successful in the multiple pass transmembrane proteins; further, also in view of the fact that there have been no reports of antibodies recognizing the extracellular region of hCL-2 although the production of hCL-1 antibody by the DNA immunization method has been reported (Gastroenterology, 139, 953, 2010), and the like, it is strongly suggested that hCL-2 antibody cannot be produced simply by using the DNA immunization method.

The DNA immunization method is a basic technique for producing an antibody against a non-denatured (native form) antigenic protein. Basically, the DNA immunization method uses cDNA encoding the full-length amino acid sequence of the protein as an immunogen. Truncation of antigenic proteins often results in an increase in the amount of antigen expression in vivo, thereby often increasing the antibody titer. However, it has been reported that there were many cases in which the produced antibody failed to recognize a non-denatured antigen, and that when multiple pass transmembrane proteins are targeted, the membrane orientation and the intracellular localization of the target protein were changed from those of the non-denatured target protein because of addition of an extra tag sequence to the N-terminal or the C-terminal of the protein.

Under such circumstances, the inventors of the present invention conducted extensive research and found that an antibody that specifically recognizes the extracellular region of Claudin-2 can be produced by devising specific methods of DNA immunization and screening. More specifically, by employing a method of using an immune construct comprising a full-length amino acid sequence of the protein with no addition of extra tag sequence to the N- or C-terminal as an antigenic protein, and using, as the immune animal, rats whose antibody titer more easily increases compared with that of mice, the inventors succeed in producing an antibody that specifically recognizes the extracellular region of Claudin-2. With further research based on this finding, the inventors completed the present invention.

More specifically, the present invention typically encompasses the aspects of the following items.

Item 1.
A monoclonal antibody that specifically binds to an extracellular region of Claudin-2.

Item 2.
The monoclonal antibody according to Item 1, wherein the monoclonal antibody recognizes a three-dimensional structure of the extracellular region of Claudin-2.

Item 3.
The monoclonal antibody according to Item 1 or 2, wherein the extracellular region is an extracellular region first loop of Claudin-2.

Item 4.
The monoclonal antibody according to any one of Items 1 to 3, wherein the monoclonal antibody comprises:
a heavy-chain variable region comprising:
heavy-chain CDR1 comprising the amino acid sequence represented by SEQ ID NO: 1 or SEQ ID NO: 2,
heavy-chain CDR2 comprising the amino acid sequence represented by SEQ ID NO: 3 or SEQ ID NO: 4, and
heavy-chain CDR3 comprising the amino acid sequence represented by SEQ ID NO: 5 or SEQ ID NO: 6; and
a light-chain variable region comprising:
light-chain CDR1 comprising the amino acid sequence represented by SEQ ID NO: 7 or SEQ ID NO: 8,
light-chain CDR2 comprising the amino acid sequence represented by SEQ ID NO: 9 or SEQ ID NO: 10, and
light-chain CDR3 comprising the amino acid sequence represented by SEQ ID NO: 11 or SEQ ID NO: 12.

Item 5.
The monoclonal antibody according to any one of Items 1 to 3, wherein the monoclonal antibody has a structure of Fab, Fab', (Fab')$_2$, Fv, scFv, sdFv, or a combination thereof.

Item 6.
The monoclonal antibody according to any one of Items 1 to 5, wherein the monoclonal antibody is a chimeric antibody or a humanized antibody.

Item 7.
The monoclonal antibody according to any one of Items 1 to 6, wherein the monoclonal antibody is IgA, IgD, IgE, IgG, IgM, or IgY.

Item 8.
A pharmaceutical composition comprising the monoclonal antibody according to any one of Items 1 to 7.

Item 9.
The pharmaceutical composition according to Item 8, wherein the pharmaceutical composition is used for the treatment of inflammatory bowel disease.

Item 10.
The pharmaceutical composition according to Item 9, wherein the inflammatory bowel disease is at least one member selected from the group consisting of ulcerative colitis, Crohn's disease, and celiac disease.

Item 11.
The pharmaceutical composition according to Item 8, wherein the pharmaceutical composition is used for the treatment of cancer.

Item 12.
The pharmaceutical composition according to Item 11, wherein the cancer is at least one member selected from the group consisting of renal cancer, colon cancer, lung cancer, and liver cancer.

Item 13.
A diagnostic marker for inflammatory bowel disease, comprising the monoclonal antibody according to any one of Items 1 to 7.

Item 14.
The marker according to Item 13, wherein the inflammatory bowel disease is at least one member selected from the group consisting of ulcerative colitis, Crohn's disease, and celiac disease.

Item 15.
A diagnostic marker for cancer, comprising the monoclonal antibody according to any one of Items 1 to 7.

Item 16.
The marker according to Item 15, wherein the cancer is at least one member selected from the group consisting of renal cancer, colon cancer, lung cancer, and liver cancer.

Item 17.
Use of the monoclonal antibody according to any one of Items 1 to 7 as a diagnostic marker for inflammatory bowel disease.

Item 18.
The use according to Item 17, wherein the inflammatory bowel disease is at least one member selected from the group consisting of ulcerative colitis, Crohn's disease, and celiac disease.

Item 19.
Use of the monoclonal antibody according to any one of Items 1 to 7 as a diagnostic marker for cancer.

Item 20.
The use according to Item 19, wherein the cancer is at least one member selected from the group consisting of renal cancer, colon cancer, lung cancer, and liver cancer.

Item 21.
A composition for examination of inflammatory bowel disease, comprising the monoclonal antibody according to any one of Items 1 to 7.
Item 22.
The composition according to Item 21, wherein the inflammatory bowel disease is at least one member selected from the group consisting of ulcerative colitis, Crohn's disease, and celiac disease.
Item 23.
A composition for examination of cancer, comprising the monoclonal antibody according to any one of Items 1 to 7.
Item 24.
The composition according to Item 23, wherein the cancer is at least one member selected from the group consisting of renal cancer, colon cancer, lung cancer, and liver cancer.
Item 25.
A substance delivery carrier for Claudin-2-expressed cells, comprising the monoclonal antibody according to any one of Items 1 to 7.
Item 26.
A method for producing the monoclonal antibody according to any one of Items 1 to 6, the method comprising the steps of:
(a) a step of introducing an expression vector comprising a polynucleotide encoding Claudin-2 into an immunized animal;
(b) a step of recovering cells having antibody producibility from the immunized animal and then performing cell fusion to prepare a hybridoma; and
(c) a step of recovering an antibody from the hybridoma, wherein the polynucleotide encoding Claudin-2 is a polynucleotide encoding the full-length amino acid sequence length of Claudin-2, and
the immunized animal is an immunized animal whose antibody titar easily increases.
Item 27.
The method according to Item 26, wherein the immunized animal is rat.

Advantageous Effects of Invention

The present invention provides a monoclonal antibody that specifically binds to an extracellular region of Claudin-2. Further, the present invention also provides a pharmaceutical composition comprising the antibody, and uses including a substance delivery carrier for Claudin-2-expressed cells comprising the antibody, and the like.

DESCRIPTION OF EMBODIMENTS

Figure 1:
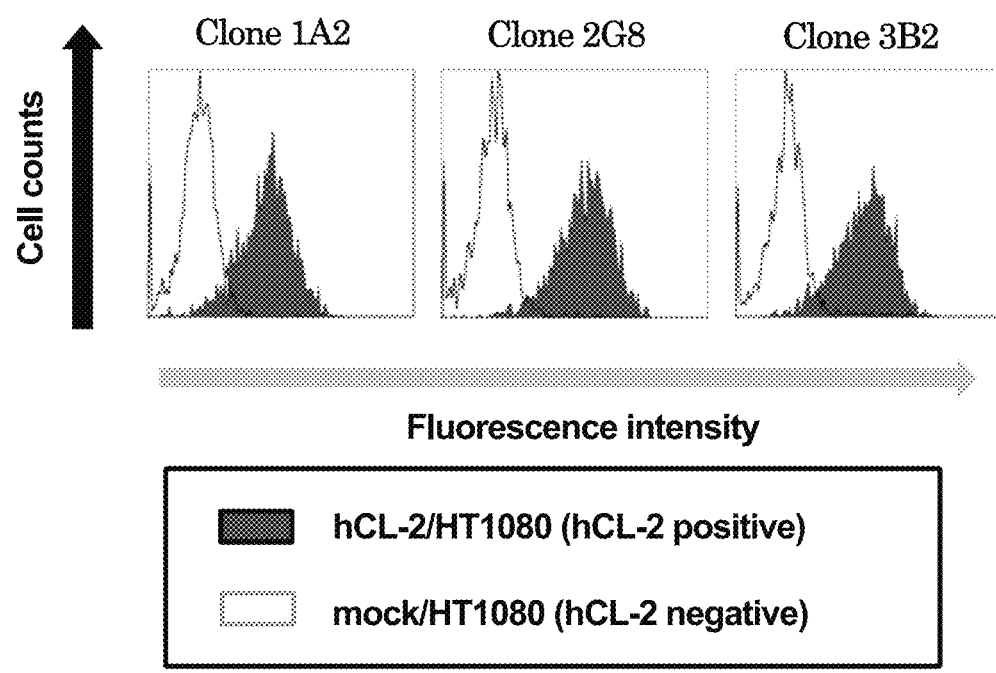
FIG. 1 is a diagram showing the results of FCM analysis performed in Example 1.

The present invention is specifically explained below. In this specification, Claudin-2 may be referred to as "CL-2".
The monoclonal antibody of the present invention is an antibody against Claudin-2 (in this specification, the antibody may also be referred to as "anti-Claudin-2 antibody" or "anti-CL-2 antibody"), and more specifically an antibody that specifically binds to an extracellular region of Claudin-2. Claudin-2 has two extracellular regions. It is known that the 28th to 78th amino acids correspond to the first loop of the extracellular region, and the 144th to 162nd amino acids correspond to the second loop of the extracellular region. The monoclonal antibody of the present invention specifically binds to an epitope contained in the 28th to 78th amino acid sequences, which correspond to the extracellular region first loop of the extracellular region. Further, the monoclonal antibody of the present invention specifically recognizes the three-dimensional structure, such as the secondary structure or the tertiary structure, instead of the primary structure, of the extracellular region first loop.
The monoclonal antibody of the present invention encompasses not only immunoglobulin (Ig) molecules but also biologically active monoclonal antibody fragments that bind to the extracellular region of Claudin-2. The fragments may be any of those having a heavy-chain and/or light-chain variable region, or those obtained by appropriately reconstituting such fragments. Examples of specific structures of the fragments include Fab, Fab', (Fab')$_2$, Fv, scFv, sdFv, and the like. Examples also include those obtained by combining these structures.
Further, the isotype of the monoclonal antibody of the present invention is not particularly limited, and examples include IgA, IgD, IgE, IgG, IgM, IgY, and the like. Among these, IgG and IgM are preferable, and IgG is particularly preferable. The subclass of IgG is not particularly limited, and examples include IgG1, IgG2, IgG2a, IgG2b, IgG3, IgG4, and the like. Among these, IgG2b is preferable.

The monoclonal antibody of the present invention is preferably an antibody comprising:
a heavy-chain variable region comprising:
heavy-chain CDR1 comprising the amino acid sequence represented by SEQ ID NO: 1 or SEQ ID NO: 2;
heavy-chain CDR2 comprising the amino acid sequence represented by SEQ ID NO: 3 or SEQ ID NO: 4; and
heavy-chain CDR3 comprising the amino acid sequence represented by SEQ ID NO: 5 or SEQ ID NO: 6, and
a light-chain variable region comprising:
light-chain CDR1 comprising the amino acid sequence represented by SEQ ID NO: 7 or SEQ ID NO: 8;
light-chain CDR2 comprising the amino acid sequence represented by SEQ ID NO: 9 or SEQ ID NO: 10; and
light-chain CDR3 comprising the amino acid sequence represented by SEQ ID NO: 11 or SEQ ID NO: 12.

Further, the monoclonal antibody of the present invention is more preferably an antibody comprising:
a heavy-chain variable region comprising:
heavy-chain CDR1 comprising the amino acid sequence represented by SEQ ID NO: 1;
heavy-chain CDR2 comprising the amino acid sequence represented by SEQ ID NO: 3; and
heavy-chain CDR3 comprising the amino acid sequence represented by SEQ ID NO: 5, and
a light-chain variable region comprising:
light-chain CDR1 comprising the amino acid sequence represented by SEQ ID NO: 7;
light-chain CDR2 comprising the amino acid sequence represented by SEQ ID NO: 9; and
light-chain CDR3 comprising the amino acid sequence represented by SEQ ID NO: 11,
or an antibody comprising:
a heavy-chain variable region comprising:
heavy-chain CDR1 comprising the amino acid sequence represented by SEQ ID NO: 2;
heavy-chain CDR2 comprising the amino acid sequence represented by SEQ ID NO: 4; and
heavy-chain CDR3 comprising the amino acid sequence represented by SEQ ID NO: 6, and
a light-chain variable region comprising:
light-chain CDR1 comprising the amino acid sequence represented by SEQ ID NO: 8;
light-chain CDR2 comprising the amino acid sequence represented by SEQ ID NO: 10; and
light-chain CDR3 comprising the amino acid sequence represented by SEQ ID NO: 12.

The monoclonal antibody having the heavy-chain variable region and the light-chain variable region may further comprise a framework region (FR) or a subregion thereof. The amino acid sequence constituting FR may be appropriately determined by a known method.

Examples of such monoclonal antibodies having the heavy-chain variable region and the light-chain variable region containing FR include an antibody comprising:
a heavy-chain variable region comprising the amino acid sequence represented by SEQ ID NO: 13 or SEQ ID NO: 14; and
a light-chain variable region comprising the amino acid sequence represented by SEQ ID NO: 15 or SEQ ID NO: 16, and preferably an antibody comprising:
a heavy-chain variable region comprising the amino acid sequence represented by SEQ ID NO: 13; and
a light-chain variable region comprising the amino acid sequence represented by SEQ ID NO: 15,
or an antibody comprising:
a heavy-chain variable region comprising the amino acid sequence represented by SEQ ID NO: 14; and
a light-chain variable region comprising the amino acid sequence represented by SEQ ID NO: 16.

The monoclonal antibody of the present invention may comprise an amino acid sequence having identity of not less than 90%, preferably not less than 95%, more preferably not less than 97%, further preferably not less than 98%, particularly preferably not less than 99% with respect to the amino acid sequences represented by SEQ ID NOS: 1 to 16, insofar as the functions thereof are not impaired. The identity of the amino acid may be calculated by a known method.

In the monoclonal antibody of the present invention, the amino acid sequences represented by SEQ ID NOS: 1 to 16 may include arbitrary mutations, insofar as the functions thereof are not impaired. "Mutation" specifically means substitution, deletion, insertion or the like. The number of mutations to be introduced into the amino acid sequences represented by SEQ ID NOS: 1 to 16 is not particularly limited insofar as the functions of the monoclonal antibody of the present invention are not impaired. For example, it is sufficient that the identity of the amino acid sequence before the introduction of the mutation with the amino acid sequence after the introduction of the mutation is not less than 90%, preferably not less than 95%, more preferably not less than 97%, further preferably not less than 98%, particularly preferably not less than 99%. The method for introducing the mutation is not particularly limited, and any known methods may be used.

When the mutation to be introduced into the amino acid sequence is a substitution, it is preferred that the substitution is a conservative substitution. In this specification, "conservative substitution" means replacing an amino acid with an amino acid having a side chain with properties similar to that of the side chain of the amino acid. Examples of conservative substitutions include substitution between amino acid residues having a basic side chain, such as lysine, arginine, and histidine, etc.; substitution between amino acid residues having an acidic side chain, such as aspartic acid and glutamic acid, etc.; substitution between amino acid residues having an uncharged polar side chain, such as glycine, asparagine, glutamine, serine, threonine, tyrosine, and cysteine, etc.; substitution between amino acid residues having a non-polar side chain, such as alanine, valine, leucine, isoleucine, proline, phenylalanine, methionine, and tryptophan. etc.; substitution between amino acid residues having a β-branched side chain, such as threonine, valine, and isoleucine, etc.; and substitution between amino acid residues having an aromatic side chain, such as tyrosine, phenylalanine, tryptophan, and histidine, etc.

Further, the monoclonal antibody of the present invention may be a chimeric antibody or a humanized antibody. "Chimeric antibody" means an antibody in which the constant region is a human-derived amino acid sequence and the variable region is an amino acid sequence derived from a biological species other than human. Further, "humanized antibody" means an antibody in which the constant region and FR of variable region are human-derived amino acid sequences and other regions are amino acid sequences derived from a biological species other than human. The biological species other than human are not particularly limited, and examples thereof include mouse, rat, guinea pig, hamster, rabbit, ostrich, monkey, chimpanzee, horse, donkey, and the like.

A method for producing the monoclonal antibody of the present invention comprises (a) a step of introducing an expression vector comprising a polynucleotide encoding Claudin-2 into an immunized animal, (b) a step of recovering cells having antibody producibility from the immunized animal and then performing cell fusion to prepare a hybridoma, and (c) a step of recovering an antibody from the hybridoma.

The DNA immunization method is a basic technique for producing an antibody against a non-denatured (native form) antigenic protein. Generally, the DNA immunization method uses cDNA encoding the full-length amino acid sequence of the protein as an immunogen. In the DNA immunization method, the antigenic protein truncation often increases the amount of antigen expression in vivo; as a result, the antibody titer tends to increase. However, it has been observed that there were many cases in which the produced antibody failed to recognize a non-denatured antigenic protein, and that when a multiple pass transmembrane protein is targeted, the membrane orientation and the intracellular localization of the target protein were changed from those of the non-denatured protein because of addition of an extra tag sequence or the like to the N-terminal or the C-terminal of the protein, and the like. Therefore, the method for producing the monoclonal antibody of the present invention is characterized by using an expression vector comprising a polypeptide encoding the full-length amino acid sequence length of Claudin-2 protein (e.g., a polypeptide encoding the full-length amino acid sequence length of Claudin-2 protein in which an extra tag sequence or the like is not added to the N-terminal or C-terminal as an immunogen), and using an immunized animal whose antibody titer tends to easily increase. The immunized animal whose antibody titer tends to easily increase is preferably an animal having an antibody titar higher than that of mice. Examples of such animals include rats. Further, the immunized animal is preferably a non-human mammal.

Steps (a) to (c) above may be performed by a known method. Further, examples of the cells having the antibody producibility used in step (b) include lymphoid cells and the like, and examples of the partners in the cell fusion include myeloma cells.

Specific examples of the method for producing the monoclonal antibody of the present invention include a method comprising immunizing a rat whose antibody titer tends to easily increase using an expression vector comprising a polypeptide encoding the full-length amino acid sequence length of Claudin-2 in which an extra tag sequence or the like is not added to the N-terminal or C-terminal, collecting the lymphoid cells from the rat, producing a hybridoma by fusing them with, for example, myeloma cells, collecting the antibodies produced by the hybridoma, and subjecting them to screening. As a more specific method, for example, the method described in the following "Examples" can be used.

The monoclonal antibody of the present invention may be used as a pharmaceutical composition. In other words, the present invention encompasses a pharmaceutical composition comprising the monoclonal antibody described above. As necessary, the pharmaceutical composition of the present invention may comprise other components, in addition to the monoclonal antibody described above. The other components are not particularly limited insofar as they are pharmaceutically acceptable. Examples include substrates, carriers, excipients, binders, disintegrants, lubricants, solvents, sweetening agents, coloring agents, flavoring agents, surfactants, moisturizers, preservatives, pH adjusters, thickening agents, and the like.

The dosage form of the pharmaceutical composition of the present invention is not limited, as long as the desired effects are obtained. The pharmaceutical composition of the present invention can be administered by any of the following administration routes: oral administration and parenteral administration (e.g., intravenous injection, intramuscular injection, subcutaneous administration, rectal administration, dermal administration, and local administration).

The dosage form of the pharmaceutical composition of the present invention for oral administration is not particularly limited. Examples include tablets, coated tablets, powders, granules, fine granules, capsules, pills, liquids, suspensions, emulsions, jellies, chewable tablets, soft tablets and the like.

Examples of the dosage forms of the pharmaceutical composition for parenteral administration include, but are not particularly limited to, injection preparations (e.g., intravenous drip infusion, intravenous injection, intramuscular injection, subcutaneous injection, and endodermic injection), external preparations (e.g., ointments, cataplasms, and lotions), pulmonary agents, suppositories, inhalants, eye drops, ophthalmic ointments, nasal drops, ear drops, and the like. For example, an injection preparation can be prepared by dissolving an antibody or cells in distilled water for injection, and optionally adding a solubilizer, a buffer, a pH adjuster, an isotonizing agent, a soothing agent, a preservative, a stabilizer, etc. The pharmaceutical composition can also be used as a freeze-dried preparation prepared before use.

The content of the monoclonal antibody in the pharmaceutical composition of the present invention is not particularly limited. For example, the content may be 0.0005 to 100 mass %, preferably 0.001 to 90 mass %, more preferably 0.01 to 80 mass %, based on the whole pharmaceutical composition of the present invention.

The dosage of the pharmaceutical composition of the present invention is not particularly limited, and may be appropriately determined in consideration of, for example, the administration form, the dosage form, the type of disease to be treated, the age of the patient, the severity of the symptoms of the patient, and the like. The dosage may be determined, for example, in the range of 0.0001 to 1000 mg/kg, or 0.001 to 100000 mg/body. The administration method of the pharmaceutical composition of the present invention is not particularly limited, and may be appropriately determined in consideration of, for example, the administration form, the dosage form, the type of disease to be treated, the age of the patient, the severity of the symptoms of the patient, and the like. For example, the pharmaceutical composition in an amount within this range may be administered once a day or divided into several doses per day (e.g., 2 to 5 times). Further, the administration intervals are also not particularly limited, and the administration may be performed, for example, every day, every other day, every week, every two weeks, every 2 to 3 weeks, every month, every two months, or every 2 to 3 months.

It is known that the expression amount of Claudin-2 increases in inflammatory bowel diseases and cancers. Claudin-2 has an effect of weakening adhesion between epithelial cells and enhancing substance permeability through intercellular gaps; therefore, the absorption of undigested food and inflammatory substances derived from intestinal bacteria through the intestinal epithelium is facilitated by the increased expression of Claudin-2, thereby worsening the condition of the inflammatory bowel disease. Further, Claudin-2 contributes to the growth and metastasis of cancers. The monoclonal antibody of the present invention has an effect of inhibiting the effects of weakening intercellular adhesion of Claudin-2, thereby suppressing a decrease in disease condition of inflammatory bowel disease. Further, the monoclonal antibody of the present invention has an antitumor effect due to antibody-dependent cytotoxic activity. Therefore, the pharmaceutical composition of the present invention may preferably be used as a pharmaceutical composition for use in the treatment of inflammatory bowel diseases or cancers.

When the pharmaceutical composition of the present invention is used for the treatment of inflammatory bowel diseases or cancers, the object to which the pharmaceutical composition of the present invention is administered is preferably an inflammatory bowel disease patient, a cancer patient, or a patient likely to have inflammatory bowel disease or cancer. The object may be a human or other mammal (non-human mammal). Examples of non-human mammals include mammals bred as pets and livestock, and examples include cats, dogs, bovines, pigs, sheep, goats, monkeys, rabbits, mice, rats and hamsters.

Examples of inflammatory bowel diseases include ulcerative colitis, Crohn's disease, celiac disease, and the like. Examples of cancers include renal cancer, colon cancer, lung cancer, liver cancer, and fibrosarcoma.

When the pharmaceutical composition of the present invention is used for the treatment of inflammatory bowel disease, the pharmaceutical composition of the present invention may contain, in addition to the monoclonal antibody of the present invention, components having an effect of treating inflammatory bowel disease (the components may hereinafter be referred to as "other components having an effect of treating inflammatory disease"). Further, the pharmaceutical composition of the present invention may be used in combination with a pharmaceutical containing other components having an effect of treating inflammatory bowel disease. Further, the pharmaceutical composition of the present invention may be a pharmaceutical composition comprising a complex obtained by binding the monoclonal antibody of the present invention described above with other components having an effect of treating inflammatory bowel disease by a known method. Examples of the other components having an effect of treating inflammatory bowel disease include infliximab, adalimumab, golimumab, certolizumab pegol, 5-aminosalicylic acid, steroids, azathioprine, tacrolimus and the like.

When the pharmaceutical composition of the present invention is used for the treatment of cancer, the pharmaceutical composition of the present invention may contain, in addition to the monoclonal antibody of the present invention, components having an effect of treating cancer (the components may hereinafter be referred to as "other components having an effect of treating cancer"). Further, the pharmaceutical composition of the present invention may be used in combination with a pharmaceutical containing other components having an effect of treating cancer. Further, the pharmaceutical composition of the present invention may be a pharmaceutical composition comprising a complex obtained by binding the monoclonal antibody of the present invention described above with other components having an effect of treating cancer by a known method.

Examples of the other components having an effect of treating cancer include cisplatin, oxaliplatin, carboplatin, nedaplatin, 5-fluorouracil, enocitabine, capecitabine, carmofur, cladribine, nivolumab, pembrolizumab, ipilimumab, cyclophosphamide, ifosfamide, melphalan, busulfan, thiotepa, nimustine, ranimustine, dacarbazine, procarbazine, temozolomide, carmustine, streptozotocin, bendamustine, sulfadiazine, sulfamethoxazole, diaphenylsulfone, methotrexate, trimethoprim, pyrimethamine, 6-mercaptopurine, azathioprine, pentostatin, thioguanine, fludarabine phosphate, cladribine, cytarabine, gemcitabine, irinotecan, nogitecan, doxorubicin, etoposide, levofloxacin, ciprofloxacin, vinblastine, vincristine, vindesine, paclitaxel, docetaxel, mitomycin C, doxorubicin, epirubicin, daunorubicin, and bleomycin.

Further, since the monoclonal antibody of the present invention specifically binds to an extracellular region of Claudin-2, the monoclonal antibody of the present invention may preferably be used to entrap Claudin-2-expressed cells. In other words, the present invention encompasses a Claudin-2-expressed cell entrapping agent comprising the monoclonal antibody described above. By using, for example, a fluorescent labeled monoclonal antibody of the present invention, for example, the Claudin-2-expressed cells may be visually distinguished. Further, since the expression amount of Claudin-2 increases in inflammatory bowel diseases and cancers, the monoclonal antibody of the present invention, which has the Claudin-2-expressed cell entrapping effects as described above, can preferably be used as diagnostic markers, compositions for examinations, and the like for inflammatory bowel diseases or cancers. In other words, the present invention also encompasses a diagnostic marker for inflammatory bowel diseases or cancers comprising the monoclonal antibody of the present invention described above, use of the monoclonal antibody of the present invention described above as a diagnostic marker for inflammatory bowel diseases or cancers, and a composition for examining inflammatory bowel diseases or cancers comprising the monoclonal antibody of the present invention described above.

Further, it is strongly suggested that the monoclonal antibody of the present invention is captured into a cell after it specifically binds to an extracellular region of Claudin-2, as shown in Example 13. Therefore, the monoclonal antibody of the present invention may be used as a carrier for delivering substances to the Claudin-2-expressed cells. In other words, the present invention also encompasses a substance delivery carrier for Claudin-2-expressed cells comprising the monoclonal antibody described above. For example, by using a complex formed by causing the monoclonal antibody of the present invention to bind to a drug, such as the other components having an effect of treating inflammatory diseases or the other components having an effect of treating cancer described above, by a known method, it becomes possible to deliver the drug exclusively to Claudin-2-expressed cells.

EXAMPLES

The present invention is described in more detail below with reference to Examples. However, the present invention is not limited to the following Examples.

Example 1 Preparation of Anti-CL-2 Antibody

The DNA immunization method is a basic technique for producing an antibody against a non-denatured (native form) antigenic protein. Generally, the DNA immunization method uses cDNA encoding the full-length amino acid sequence of the protein as an immunogen. In the DNA immunization method, the antigenic protein truncation often increases the amount of antigen expression in vivo; as a result, the antibody titer tends to increase. However, it has been observed that there were many cases in which the produced antibody failed to recognize a non-denatured antigenic protein, and that when a multiple pass transmembrane protein is targeted, the membrane orientation and the intracellular localization of the target protein were changed from those of the non-denatured protein because of addition of an extra tag sequence or the like to the N-terminal or the C-terminal of the protein, and the like.

Accordingly, in the preparation of a monoclonal antibody against CL-2 (hereinafter referred to as "anti-CL-2 antibody"), an immune construct consisting of the full-length amino acid sequence of the protein without adding any extra tag sequence or the like to the N-terminus or C-terminus was used as an antigen, and rats whose antibody titer more easily increases compared with that of mice were used as an immune animal.

1) Immunization

Twenty Wister rats were subcutaneously immunized with a human CL-2 expression plasmid, and serum antibody titer was determined by flow cytometry (FCM) analysis. Seven rats confirmed to have an increased antibody titer were subjected to final immunization (boosting).

2) Cell Fusion

After the final immunization, lymphoid cells were recovered from the rats and subjected to cell fusion with mouse myeloma (P3U1) to produce hybridomas. The hybridomas were then seeded in five 96-well plates and cultured in a culture medium of the following composition at 37° C. in a 5% $CO_2$ atmosphere for 14 days.

Composition of Culture Medium

D-MEM (Wako, 044-29765)+10% FCS (Hyclone), 10% BM condimed H1 Hybridoma cloning supplement (Roche, 1088947), 1×HAT supplement (Invitrogen, 21060017), 1×Penicillin/Streptomycin (Wako, 168-23191), and 1×L-Glutamine (Wako, 073-05391).

3) Primary Screening

After culturing, culture supernatants were collected from all the plate wells. For primary screening, human CL-2-expressing HT1080 cells (hCL-2/HT1080 cells) and control HT1080 cells (mock/HT1080 cells) were used. These cells and their preparation methods are reported in Li et al., J Pharmacol Exp Ther, 351, pp. 206-213, 2014. hCL-2/HT1080 and mock/HT1080 cells cultured in cell culture plates were recovered by trypsin treatment. After the collected hybridomas culture supernatants were added to these cells and the cells were stained using a PE-labeled anti-rat IgG antibody as a secondary antibody, FCM analysis was performed.

4) Secondary Screening

Eighteen clones confirmed to be positive in the primary screening were expanded from 96-well plates to 24-well plates and cultured at 37° C. in a 10% $CO_2$ atmosphere. After culturing, culture supernatants were collected from all the wells. Thereafter, hCL-2/HT1080 cells and mock/HT1080 cells were stained with the culture supernatants and PE-labeled anti-rat IgG antibody, and FCM analysis was performed.

5) Limiting Dilution and Tertiary Screening

Hybridomas were recovered from 5 wells confirmed to be positive in the secondary screening, and each hybridoma was seeded at 1.2 cells/well in one 96-well plate (5 plates in total) and cultured at 37° C. in a 10% $CO_2$ atmosphere for 12 days. Hybridomas before limiting dilution were also simultaneously cultured in 6-well plates under the same conditions as above and used as backups. After culturing, 10 clones each were selected from single colony-formed wells of each plate. hCL-2/HT1080 cells and mock/HT1080 cells were stained with the culture supernatants and PE-labeled anti-rat IgG antibody, and FCM-analysis was performed.

6) Isotype Analysis

Three clones (designated as 1A2, 2G8, and 3B2) confirmed to be positive in the tertiary screening were sequentially expanded in 24-well plates and 6-well plates at 37° C. in a 10% $CO_2$ atmosphere, and cultured. After culturing, culture supernatants were collected from all the wells, and the class and subclass of antibodies in the culture supernatants were determined using a rat immunoglobulin isotyping ELISA kit (BD). Table 1 below shows the results of isotype analysis.

TABLE 1

| Clone | Isotype |
|---|---|
| 1A2 | IgG2b |
| 2G8 | IgG2b |
| 3B2 | IgM |

7) Final Screening

After the determination of subclasses, one single-subclass well with a strong shift intensity in tertiary screening was selected, and expansion culture in a 150-mm dish was performed in a culture medium of the following composition.

Composition of Culture Medium

D-MEM (Wako, 044-29765)+10% FCS (Hyclone), 3% BM condimed H1 Hybridoma cloning supplement (Roche, 1088947), 1XHAT supplement (Invitrogen, 21060017), and 1×Penicillin/Streptomycin (Wako, 168-23191).

After culturing, each hybridoma was recovered, and three cell stocks were produced using a Cellbanker (serum type) and stored at −80° C. Further, simultaneous with the expansion culture, culturing was performed in 150-mm dishes until overgrowth, and each culture supernatant (about 20 mL) was then collected and stored at −20° C.

Each hybridoma and each hybridoma culture supernatant stored by these procedures are hereinafter referred to as "hybridoma produced in Example 1" and "hybridoma culture supernatant produced in Example 1," respectively. When the hybridoma and the hybridoma culture supernatant are described with a clone name, for example, "clone 1A2" is referred to as "hybridoma 1A2 produced in Example 1" and "hybridoma culture supernatant 1A2 produced in Example 1."

hCL-2/HT1080 cells and mock/HT1080 cells were stained with the hybridoma culture supernatants (1A2 and 2G8 and 3B2) prepared above and PE-labeled anti-rat IgG antibody, and FCM analysis was performed. FIG. 1 shows the results of the FCM analysis.

As is apparent from FIG. 1, shifts indicating that hybridomas were positive were confirmed in all the three hybridoma culture supernatants 1A2, 2G8 and 3B2 prepared above.

Example 2: Analysis of Binding Specificity of Anti-CL-2 Antibody

Figure 2:
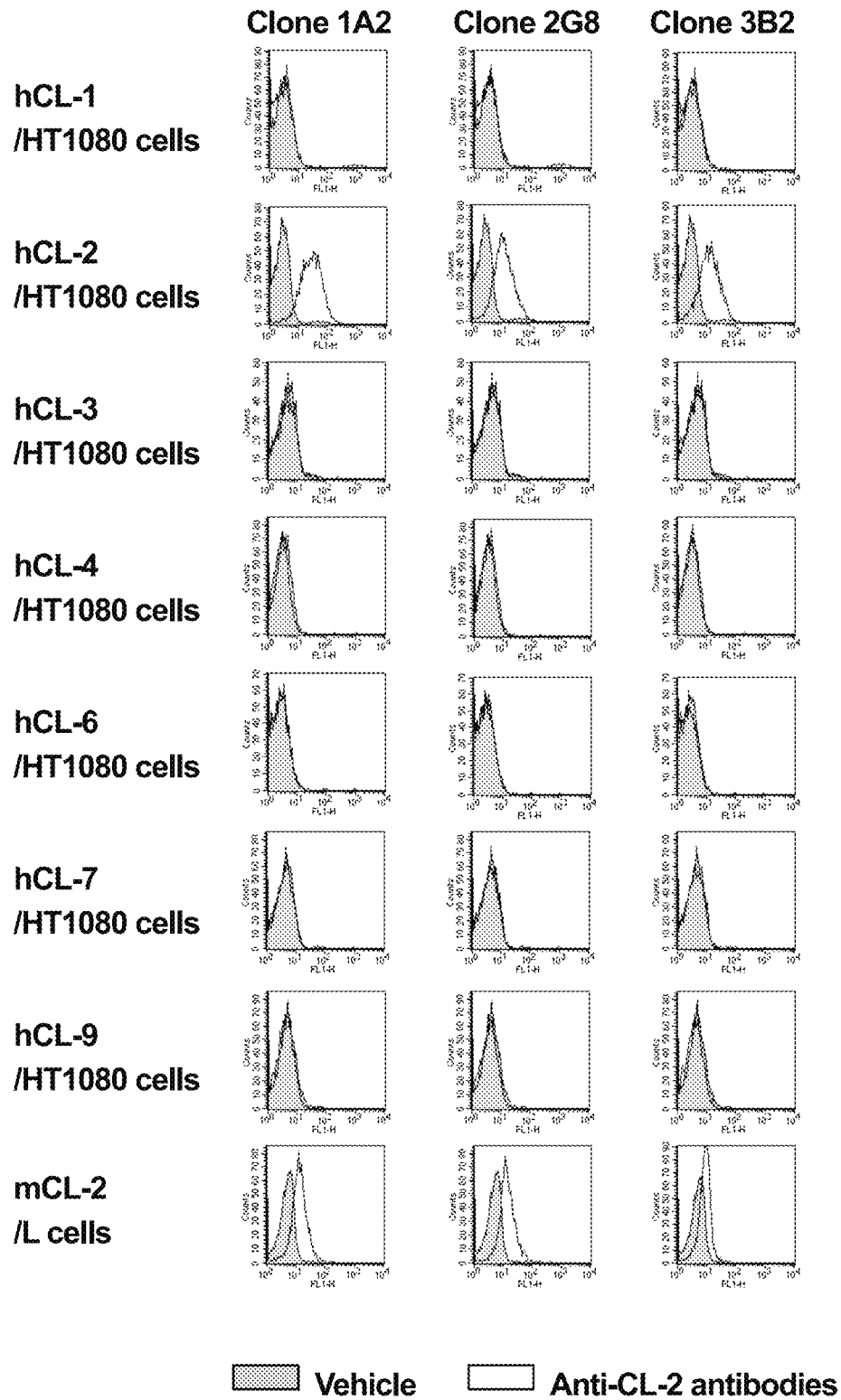
FIG. 2 is a diagram showing the results of FCM analysis performed in Example 2.

Human CL-1 expressing HT1080 cells (hCL-1/HT1080 cells), human CL-2 expressing HT1080 cells (hCL-2/HT1080 cells), human CL-3 expressing HT1080 cells (hCL-3/HT1080 cells), human CL-4 expressing HT1080 cells (hCL-4/HT1080 cells), human CL-6 expressing HT1080 cells (hCL-6/HT1080 cells), human CL-7 expressing HT1080 cells (hCL-7/HT1080 cells), human CL-9 expressing HT1080 cells (hCL-9/HT1080 cells), and mouse CL-2 expressing L cells (mCL-2/L cells) were individually seeded in 96-well plates at a concentration of 5.0×10$^5$ per sample. After the hybridoma culture supernatants prepared in Example 1 (1A2, 2G8, and 3B2) were individually added and stirred, the resulting mixtures were allowed to stand on ice for 1 hour. After washing with 0.2% BSA-PBS once, goat anti-rat IgG (H+L)-FITC antibody (KPL) diluted with 1% BSA-PBS was added and stirred, and the resulting mixtures were allowed to stand on ice for 30 minutes. After washing with 0.2% BSA-PBS once, PI (Mitenyi Biotec) diluted with 1% BSA-PBS to a final concentration of 5 μg/mL was added, and FCM analysis was performed. FIG. 2 shows the results of the FCM analysis.

As is apparent from FIG. 2, all the three hybridoma culture supernatants 1A2, 2G8, and 3B2 prepared in Example 1 were confirmed to have no affinity to hCL-1/HT1080 cells, hCL-3/HT1080 cells, hCL-4/HT1080 cells, hCL-6/HT1080 cells, hCL-7/HT1080 cells, and hCL-9/HT1080 cells, and have specific affinity to hCL-2/HT1080 cells.

Further, all the three hybridoma culture supernatants 1A2, 2G8, and 3B2 prepared in Example 1 were also confirmed to have affinity to mCL-2/L cells. The above results suggest that the anti-CL-2 antibody has cross-reactivity with human CL-2 and mouse CL-2, and can also be used in experimental systems using mice (for example, assessment of efficacy and safety of the antibody).

Example 3: Analysis of Sequence of Variable Region of Anti-CL-2 Antibody

Using TRIzol (Invitrogen), mRNAs were recovered from hybridomas 1A2 and 2G8 produced in Example 1, and purified. Using the recovered mRNAs as templates, cDNAs were synthesized using a cDNA amplification kit (Clontech). Using the synthesized cDNAs as templates, PCR was performed using KOD-plus- (TOYOBO) to individually amplify the genes of heavy-chain variable (VH) and light-chain variable (VI) regions. After the PCR, PCR products were separated and purified by electrophoresis, and ligated into pUC118HincII/BAP using a Mighty Cloning Reagent set (Takara). Competent cell DH-5α was transformed by the ligation products, and the formed independent *E. coli* clones were recovered. In the selection of *E. coli* clones, Blue-White selection was performed by applying X-gal and IPTG to LA plates to efficiently select clones having PCR products inserted thereinto. The recovered *E. coli* clones were cultured and plasmid DNAs were recovered. The target gene sequences were then analyzed by sequence analysis. Tables 2 and 3 below show the amino acid sequences of the variable regions obtained from the analysis results.

TABLE 2

| | FR1 | CDR1 | FR2 | CDR2 | FR3 | CDR3 | FR4 |
|---|---|---|---|---|---|---|---|
| Heavy-chain | | | | | | | |
| 1A2 | QVKLL QSGAA LVKPG DSMK MSCKA SGYTF T | HDII H | WV RQ SH GKS LE WI G | YINP YNG GTN YNE K | FKTKAT MTVDKP SSTAYLE LTRVSSE ASAIYYC AT | GSF DY | WGQ GVM VTV SSA |
| 2G8 | QVNLL QSGAA LVKPG ASVRL SCRVS GYSFT | VSFL H | WV KQ SH GKS LE WI G | YINP YSG SPN YNE K | FKSKTTL TVDKSTS TAYMELS GLTSEDS ASYYCT | NWD Y | WGQ GVM VTV SSA |
| Light-chain | | | | | | | |
| 1A2 | DVVLT QTPGS LSLAIG QSASI SC | KSS QSLL GTS GKT FLN | WIL QRP GQS PERL IY | QVS KLY S | EVPDRF SGSGSE TEFTLK ISRVEA EDLGVY YC | WQGI HFPH T | FGA GTK LELK R |
| 2G8 | DVVM TQTPV SLSLAI GQPAS ISC | KSS QS LLGS SGK TFL N | WIL QRP GQS PKR LIY | QVS TLY S | EVPDRF SGSGSE TEFTLK ITRVEA EDLGVY YC | WQGI HFPH T | FGA GTK LELK R |

TABLE 3

| Clone | 1A2 | | 2G8 | |
|---|---|---|---|---|
| Name | Heavy-chain | Light-chain | Heavy-chain | Light-chain |
| CDR1 | SEQ ID NO: 1 | SEQ ID NO: 7 | SEQ ID NO: 2 | SEQ ID NO: 8 |
| CDR2 | SEQ ID NO: 3 | SEQ ID NO: 9 | SEQ ID NO: 4 | SEQ ID NO: 10 |
| CDR3 | SEQ ID NO: 5 | SEQ ID NO: 11 | SEQ ID NO: 6 | SEQ ID NO: 12 |
| Variable region | SEQ ID NO: 13 | SEQ ID NO: 15 | SEQ ID NO: 14 | SEQ ID NO: 16 |

Example 4: Production of Anti-CL-2 Human-rat Chimeric Antibody

1) Production of Expression Vector

In order to add the AgeI site and BsiWI site to the light-chain variable regions of anti-CL-2 antibodies 1A2 and 2G8 and add the EcoRI site and NheI site to the heavy-chain variable regions of anti-CL-2 antibodies 1A2 and 2G8, the VI and VH of the variable regions of the antibodies were amplified by the PCR method. After the PCR, PCR products were separated and purified by electrophoresis and treated with restriction enzymes (VI: AgeI and BsiWI; VH: EcoRI and NheI). The AgeI site, BsiWI site, EcoRI site, and NheI site present on the multi-cloning site of a cloning vector including human constant regions (VI: pFUSE2-CLIg-hk, VH: pFUSE-CHIg-hG1) were cleaved with restriction enzymes (VI: AgeI and BsiWI, VH: EcoRI, and NheI), and ligated with the PCR products cleaved with the restriction enzymes. Competent cell DH-5α was transformed by ligation products. After the formed independent *E. coli* clones were cultured and plasmid DNA was recovered, VI: pFUSE2-CLIg-hk-anti-CL-2 and VH: pFUSE-CHIg-hG1-anti-CL-2 were obtained by restriction enzyme analysis and sequencing analysis.

2) Production and Purification of Anti-CL-2 Chimeric Antibody 150 mL of CHO-S cells adjusted to $5\times10^5$ cells/mL were placed in a flask and cultured at 37° C. in an 8% $CO_2$ atmosphere overnight. Further, 93 µg of pFUSE2-CLIg-hk-anti-CL-2 and 75 µg of pFUSE-CHIg-hG1-anti-CL-2 produced above in item 1) were mixed, and OptiPRO SFM was added to make a volume of 3 mL, and stirred. 187.5 µL of Free Style MAX Reagent (Invitrogen) and 2812.5 µL of OptiPRO SFM were added to another microtube and inverted to form a mixture. After the resulting mixture was added to the expression vector solution and allowed to stand at ordinary temperature for 10 minutes, the total amount of the above mixture was added to a flask containing CHO-S cells. Culturing was then performed at 37° C. in an 8% $CO_2$ atmosphere for 6 days, and supernatants were collected.

The collected supernatants were centrifuged at 100×g for 5 minutes and passed through a 0.45 µm filter. After the HiTrap Protein G HP (GE Healthcare) was washed with 5 mL of MilliQ water, column equilibration was performed with 10 mL of 0.02 M phosphate buffer. After the sample was passed through the column, the column was washed with 20 mL of 0.02 M phosphate buffer and eluted with 5 mL of 0.1 M Glycine-HCl. During the elution, 0.5-mL portions of the eluate were collected in microtubes in which 37.5 µL of 1M Tris-HCL had been placed beforehand. The buffer for the sample after elution was replaced with PBS using a PD-10 column (GE Healthcare).

Figure 3:
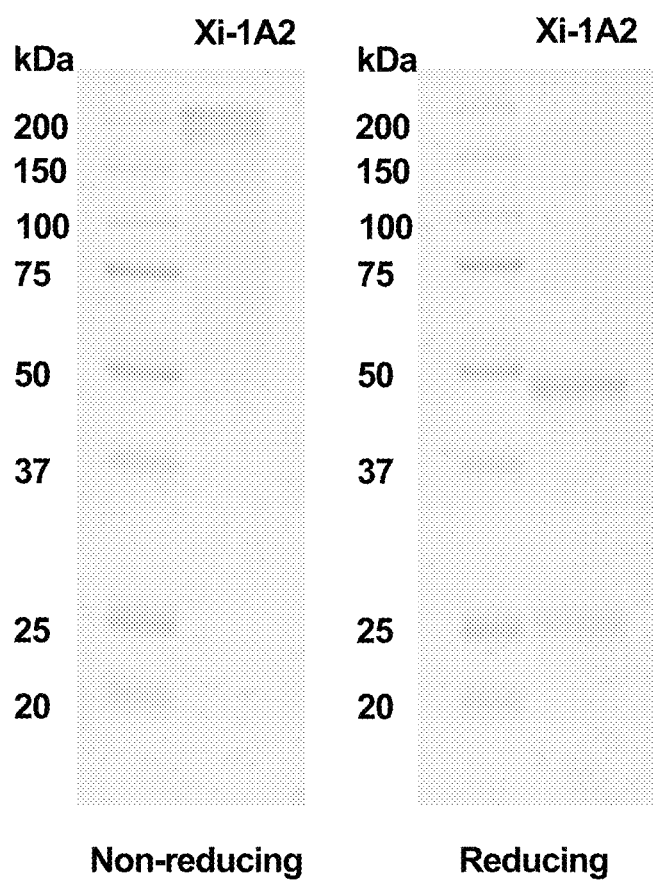
FIG. 3 is a diagram showing the results of SDS-PAGE performed in Example 4.
Figure 3:
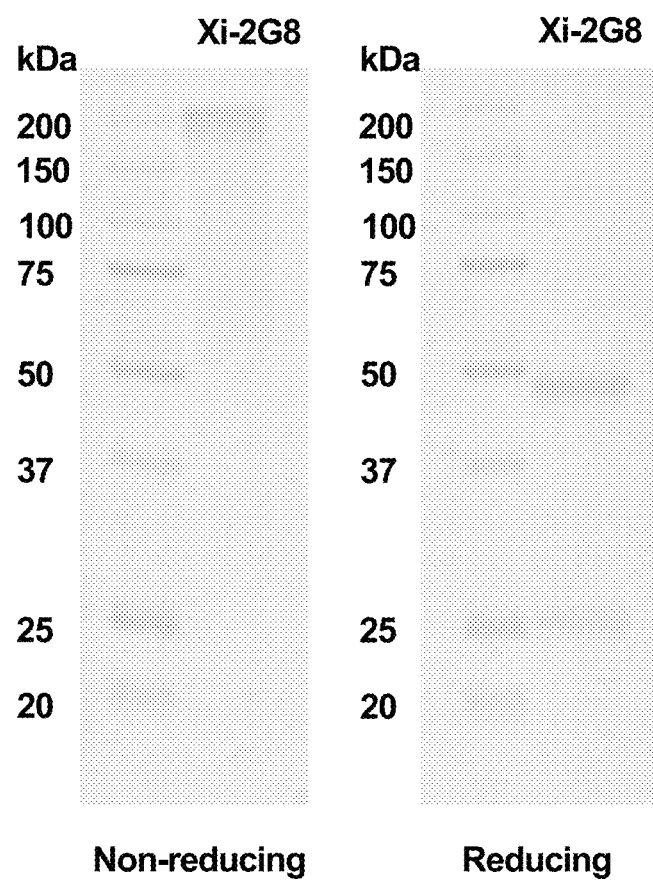

The molecular weight of the protein solution obtained by the method described above was confirmed by SDS-PAGE under non-reducing conditions and under reducing conditions. The protein concentrations were also determined by the absorbance method. FIG. 3 shows the results of SDS-PAGE.

The antibody solutions obtained by these procedures are hereinafter referred to as "anti-CL-2 chimeric antibody produced in Example 4," "anti-CL-2 human-rat chimeric antibody," or simply as "anti-CL-2 chimeric antibody." Further, when these are described with a clone name, for example, "clone 1A2" is referred to as "anti-CL-2 chimeric antibody 1A2 produced in Example 4," "anti-CL-2 human-rat chimeric antibody 1A2 produced in Example 4," and "anti-CL-2 chimeric antibody 1A2."

As is apparent from FIG. 3, regardless of whether the anti-CL-2 chimeric antibody 1A2 or the anti-CL-2 chimeric antibody 2G8a was used, a band was confirmed on the high molecular weight side (around 200 kDa) under non-reducing conditions, and bands were confirmed at about 50 kDa and about 25 kDa under reducing conditions. The results confirmed that anti-CL-2 chimeric antibodies 1A2 and 2G8 were purified.

Figure 4:
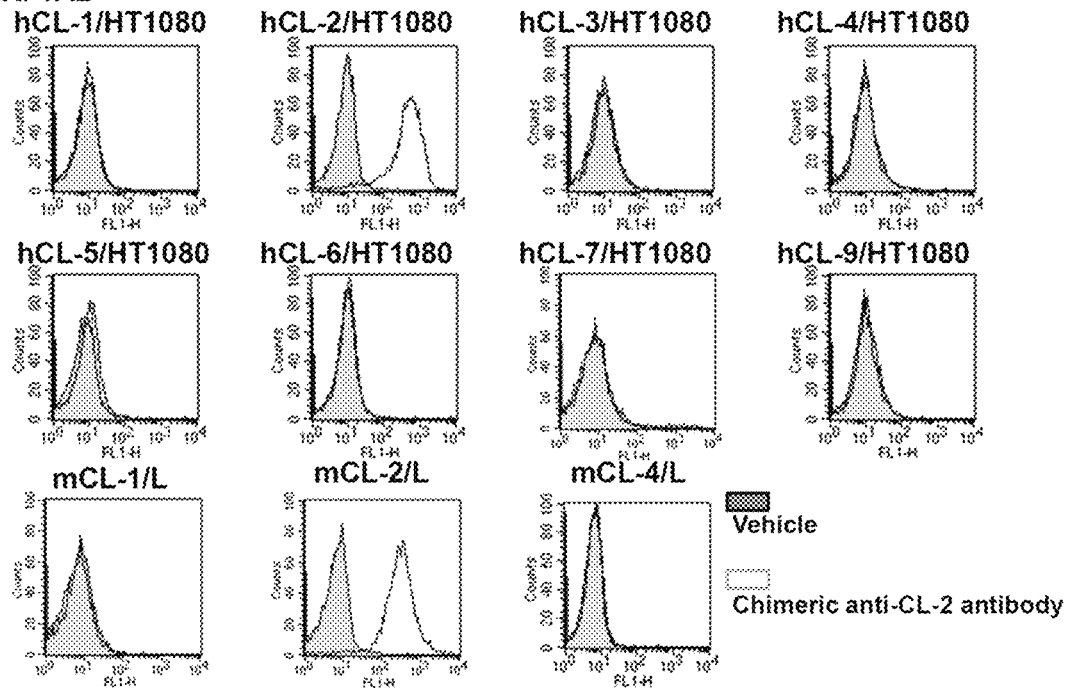
FIG. 4 is a diagram showing the results of FCM analysis performed in Example 5.
Figure 4:
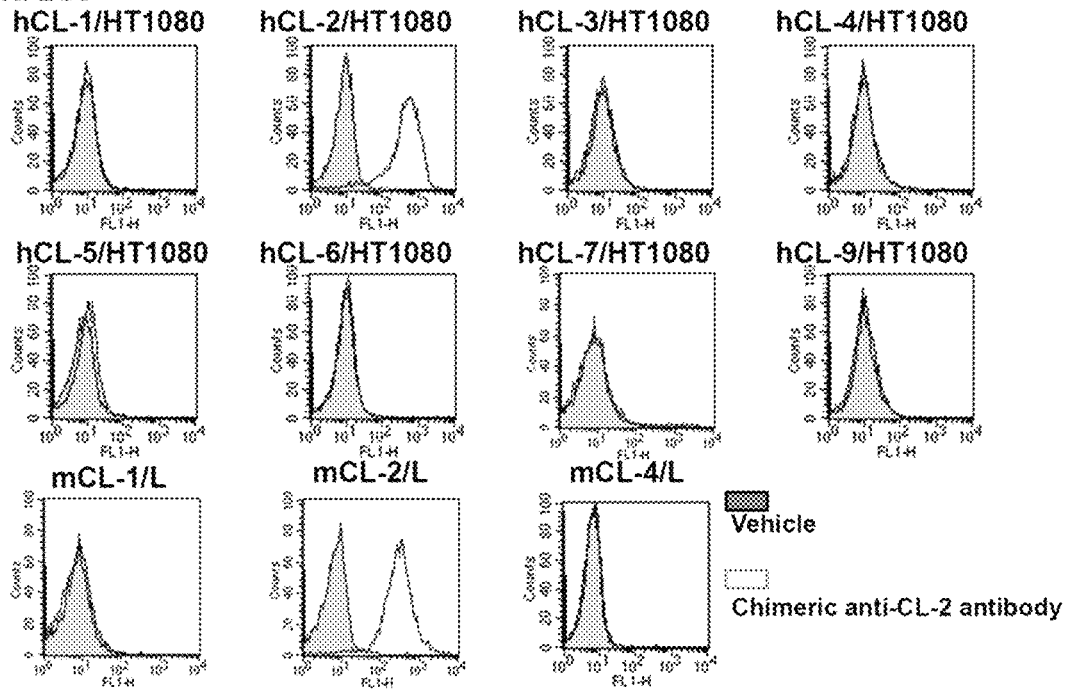

Example 5: Confirmation of Binding Specificity of Anti-CL-2 Human-Rat Chimeric Antibody hCL-1/HT1080 cells, hCL-2/HT1080 cells, hCL-3/HT1080 cells, hCL-4/HT1080 cells, human CL-5 expressing HT1080 cells (hCL-5/HT1080 cells), hCL-6/HT1080 cells, hCL-7/HT1080 cells, and hCL-9/HT1080 cells, mouse CLDN1 expressing L cells (mCL-1/L cells), mCL-2/L cells, and mouse CL4 expressing L cells (mCL-4/L cells) were individually recovered by trypsin treatment. The anti-CL-2 chimeric antibodies 1A2 and 2G8 (5 µg/mL) produced in Example 4 were individually added in an amount of 100 µL to the various cells at a concentration of $5.0\times10^5$ cells/sample, and stirred, and the resulting mixtures were allowed to stand on ice for 1 hour. Subsequently, after washing with 0.2% BSA-PBS once, goat anti-human IgG (H+L)-FITC antibody (Jackson ImmunoResearch) diluted with 1% BSA-PBS was added and stirred, and the resulting mixtures were allowed to stand on ice for 30 minutes. After washing with 0.2% BSA-PBS once, PI diluted with 1% BSA-PBS to a final concentration of 5 µg/mL was added, and FCM analysis was performed. FIG. 4 shows the results of FCM analysis.

As is apparent from FIG. 4, anti-CL-2 chimeric antibodies 1A2 and 2G8 were confirmed to have no affinity to hCL-1/HT1080 cells, hCL-3/HT1080 cells, hCL-4/HT1080 cells, hCL-5/HT1080 cells, hCL-6/HT1080 cells, hCL-7/HT1080 cells, and hCL-9/HT1080 cells, and have specific affinity to hCL-2/HT1080 cells. Further, anti-CL-2 chimeric antibodies 1A2 and 2G8 were confirmed to have no affinity to mCL-1/L cells and mCL-4/L cells, and have specific affinity to mCL-2/L cells. The above results showed that anti-CL-2 chimeric antibodies 1A2 and 2G8 retain the binding specificity of anti-CL-2 antibodies 1A2 and 2G8, respectively, and that the cloned CDR-regions are involved in binding to CL-2.

Example 6: Purification of Anti-CL-2 Antibody

1) Preparation of Mouse Ascites Fluid

The hybridomas 1A2 and 2G8 produced in Example 1 were individually transplanted into the peritoneal cavity of nude mice at 0.5 to $1.0\times10^7$ cells/mouse. In order to promote ascites fluid formation, pristane was administered in an amount of 500 µL/mouse by the day before hybridoma transplantation. From day 10 to day 14 after the hybridoma transplantation, ascites fluid was collected one or more times. The collected ascites fluid was centrifuged, and $NaN_3$ (final concentration: 0.05%) was added to the collected supernatants, followed by being stored at 4° C. until use for purification.

2) IgG Purification

Figure 5:
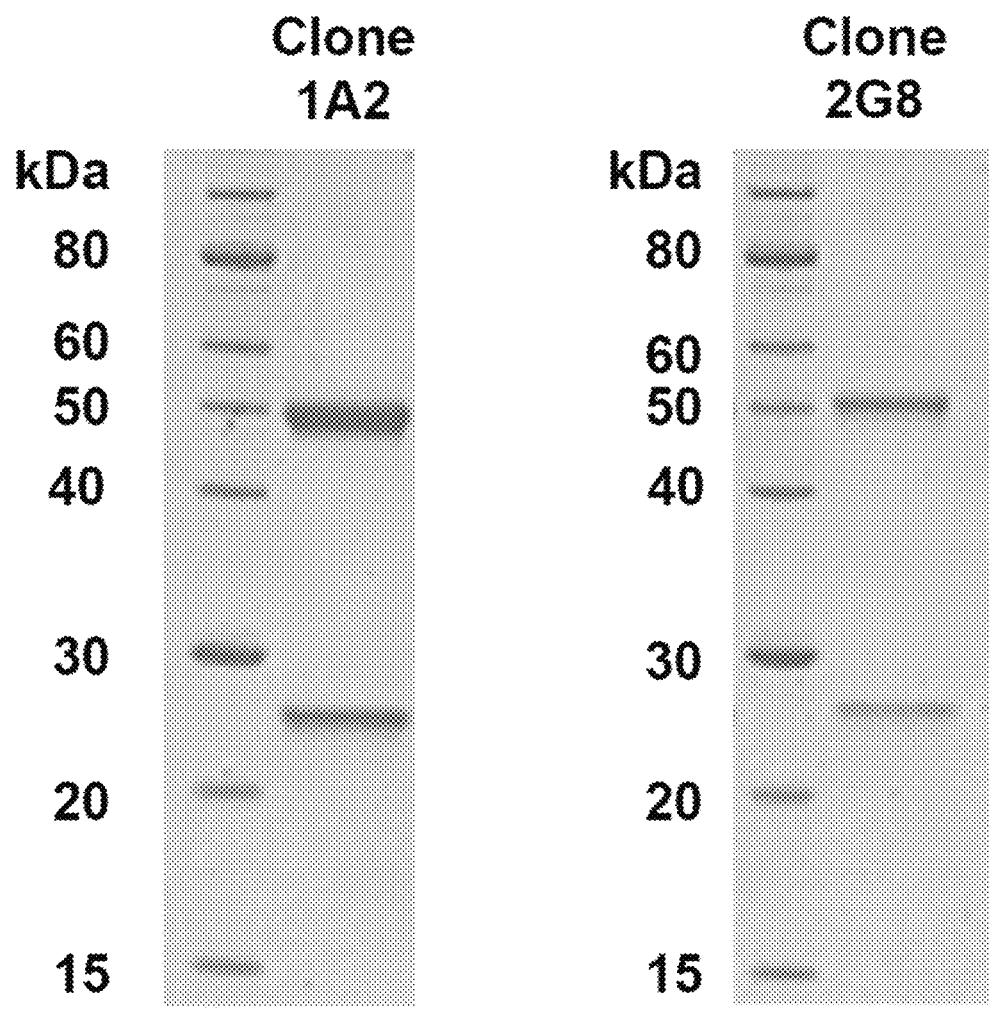
FIG. 5 is a diagram showing the results of SDS-PAGE performed in Example 6.

The ascites fluid collected from IgG2b clones (1A2 and 2G8) was purified. The ascites fluid was applied to a protein G Sepharose column (GE) pretreated with phosphate buffer. The column was then washed with phosphate buffer, and the target protein was eluted with elution buffer (0.1M Glycine-HCl, pH 3.0). The solution after elution was immediately neutralized with a small amount of 1M Tris-HCl (pH 7.0). Further, the neutralized solution was dialyzed with phosphate buffer for buffer replacement. After the dialysis, the dialysate was filtered through a 0.2 µm filter and then aseptically dispensed. A portion of the resulting target protein solution was subjected to SDS-PAGE under reducing conditions in a usual manner to confirm the molecular weight. The protein concentration was determined by the absorbance method. FIG. 5 shows the results of SDS-PAGE.

The antibody solution obtained by these procedures is hereinafter referred to as "anti CL-2 antibody produced in Example 6," or simply as "anti CL-2 antibody." When these are described with a clone name, for example, "clone 1A2" is referred to as "anti-CL-2 antibody 1A2 produced in Example 6," "anti-CL-2 antibody 1A2," or the like.

As is apparent from FIG. 5, heavy-chain (about 50 kDa) and light-chain (about 25 kDa) bands were confirmed in both of the anti-CL-2 antibodies 1A2 and 2G8.

Figure 6:
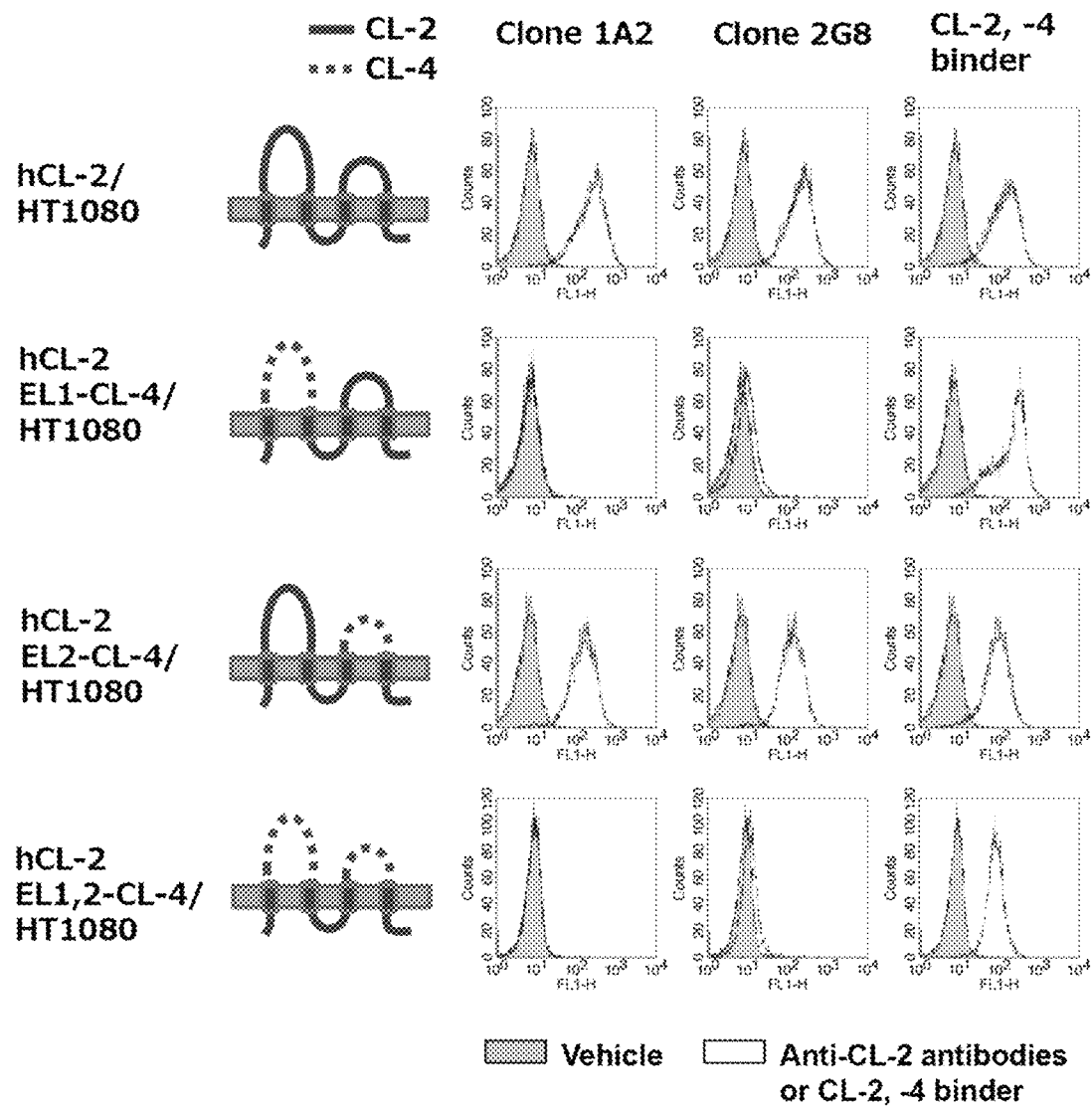
FIG. 6 is a diagram showing the results of FCM analysis performed in Example 7.

Example 7: Analysis of Epitope of Anti-CL-2 Antibody hCL-2/HT1080 cells; HT1080 cells in which the first loop of the extracellular region of hCL-2 (amino acids 28-78) was replaced with the first loop of the extracellular region of hCL-4 (CL-2 EL1-CL-4/HT1080 cells); HT1080 cells in which the second loop of the extracellular region of hCL-2 (amino acids 144-162) was replaced with the second loop of the extracellular region of hCL-4 (CL-2 EL2-CL-4/HT1080 cells); and HT1080 cells in which the first and second loops of the extracellular region of hCL-2 were replaced with the first and second loop of the extracellular region of hCL-4 (hCL-2 EL1, 2-CL-4/HT1080 cells) were individually recovered by trypsin treatment. The CL-2 antibodies 1A2 and 2G8 (adjusted to 5 μg/mL) prepared in Example 6 were individually added in an amount of 100 μL to the cells at $5.0 \times 10^5$ cells/sample and stirred, and the resulting mixtures were allowed to stand on ice for 1 hour. After washing with 0.2% BSA-PBS once, goat anti-rat IgG (H+L)-antibody FITC (KRL) diluted with 1% BSA-PBS was added and stirred, and the resulting mixtures were allowed to stand on ice for 30 minutes. After washing with 0.2% BSA-PBS once, FCM analysis was performed. FIG. 6 shows the results of FCM analysis. In this example, hCL-2 and hCL-4 binding molecule (CL-2, -4 binder) was used as a positive control, and anti-6×His tag monoclonal antibody (Pierce) and goat anti-mouse IgG (H+L)-FITC antibody (Abcam plc.) were used to detect the CL-2, -4 binder. The CL-2, -4 binder is a polypeptide (m19) having a molecular weight of about 14 kDa, and the method for producing the CL-2, -4 binder is reported in Takahashi et al., Biomaterials, 33, pp. 3464-3474, 2012.

As is apparent from FIG. 6, anti-CL-2 antibodies 1A2 and 2G8 were both confirmed to retain affinity to hCL-2 EL2-CL-4/HT1080 cells, whereas affinity of anti-CL-2 antibodies 1A2 and 2G8 to hCL-2 EL1-CL-4/HT1080 cells was lost. These results suggest that anti-CL-2 antibodies 1A2 and 2G8 specifically bind to the first loop of the extracellular region of CL-2.

Figure 7:
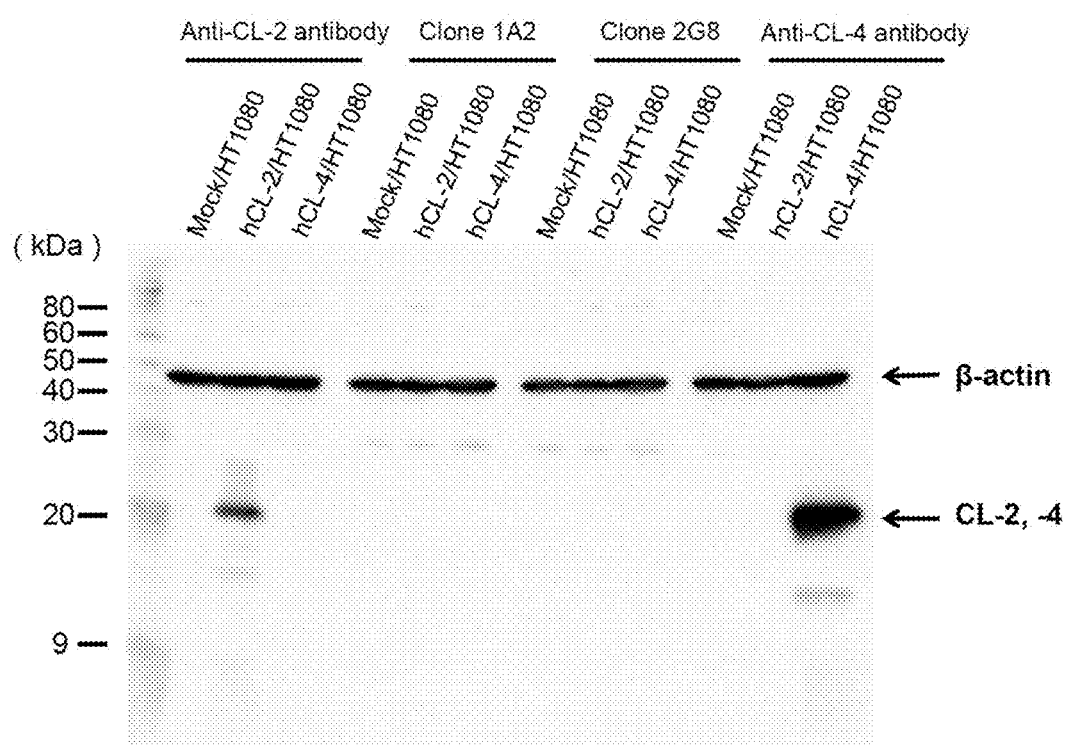
FIG. 7 is a diagram showing the results of Western blotting analysis performed in Example 8.

Example 8: Analysis of Affinity of Anti-CL-2 Antibodies to Denatured CL-2 Protein hCL-2/HT1080 cells, hCL-4/HT1080 cells, and mock/HT1080 cells were recovered. Western blotting analysis was performed using cell lysates produced. Each cell lysate was prepared by suspending cells in PBS containing a protease inhibitor (Nacalai tesque, Inc.) and 1% Triton-X and then disrupting the cells by sonication. After SDS-PAGE was performed using the cell lysates and polyacrylamide gel, treatment was performed with a TRANS-BLOT SD SEMI-DRY TRANSFER CELL (Bio-Rad Laboratories) at 240 mA for 20 minutes to thereby transfer the proteins onto a polyvinylidene difluoride (PVDF) membrane. After the transfer, the PVDF membrane was immersed in 5% skim milk-T-TBS and shaken at room temperature for 2 hours for blocking. After washing with T-TBS, a reaction with a primary antibody: a commercially available mouse anti-CL-2 antibody (Invitrogen), anti-CL-2 antibody 1A2, anti-CL-2 antibody 2G8, or a commercially available mouse anti-CL-4 antibody (Invitrogen) was allowed to proceed for 2 hours. A reaction with a secondary antibody: goat anti-mouse IgG HRP conjugated (Millipore) or goat anti-rat IgG HRP conjugated (R&D Systems) was then allowed to proceed for 1 hour. The various antibodies used above were in the form of 5% skim milk-T-TBS solutions. After washing with T-TBS, Chemi-Lumi One L (Nakcalai Tesque) or Chemi-Lumi One Super (Nakcalai Tesque) was used to develop bands, and detection was performed using Image Quant LAS 4010 (GE Healthcare Bio-Sciences Corp). FIG. 7 shows the results of Western blotting analysis.

As can be seen from FIG. 7, a CL-2 band was confirmed in the commercially available mouse anti-CL-2 antibody, whereas no CL-2 band was detected in anti-CL-2 antibody 1A2 and anti-CL-2 antibody 2G8. Since the mouse anti-CL-2 antibody used in this example is an antibody that recognizes the primary structure of the intracellular region of CL-2, the results suggest that anti-CL-2 antibody 1A2 and anti-CL-2 antibody 2G8 recognize a three-dimensional structure, rather than the primary structure of the extracellular region of CL-2.

Example 9: Analysis of TJ Barrier Control Activity of Anti-CL-2 Antibody

Caco-2 cells, commonly used as a human intestinal epithelial model, were seeded at $8 \times 10^4$ cells/200 μL in the top wells of trans-well (Corning), whereas 700 μL of medium was added to the bottom wells thereof. Culturing was performed at 37° C. in a 5% $CO_2$ atmosphere. The transepithelial electrical resistance (TEER) value, which is an indicator of epithelial barrier function, was then measured with Millicell-ERS (MILLIPORE) every other day. After the medium was replaced with fresh medium, culturing was continued. Ten days after cell seeding, when the TEER value was stabilized, the medium of the precultured cells was removed. 100 μL of medium was added to the top wells, whereas anti-CL-2 antibody solutions each prepared by adjusting anti-CL-2 antibody 1A2 or 2G8 to 10 μg/mL in medium, a rat IgG antibody solution prepared by adjusting rat IgG antibody to 10 μg/mL in medium, a 20 μg/mL solution of a molecule (m19) known to reduce a TJ modulator (Tight Junction (TJ)) barrier function: Takahashi et al., Biomaterials, 33, pp. 3464-3474, 2012), and a medium were individually added in an amount of 600 μL to the bottom wells. Culturing was performed at 37° C. in a 5% $CO_2$ atmosphere. 0, 6, 12, 18, and 24 hours after adding these various solutions, TEER values were measured. The medium of the top wells and antibody solutions of the bottom wells were then removed, and the wells were washed with PBS. 100 μL of medium was newly placed into the top wells, and 600 μL of medium was newly placed into the bottom wells. After 12 hours, TEER values were measured. FIG. 8A shows the results of TEER measurement.

Figure 8:
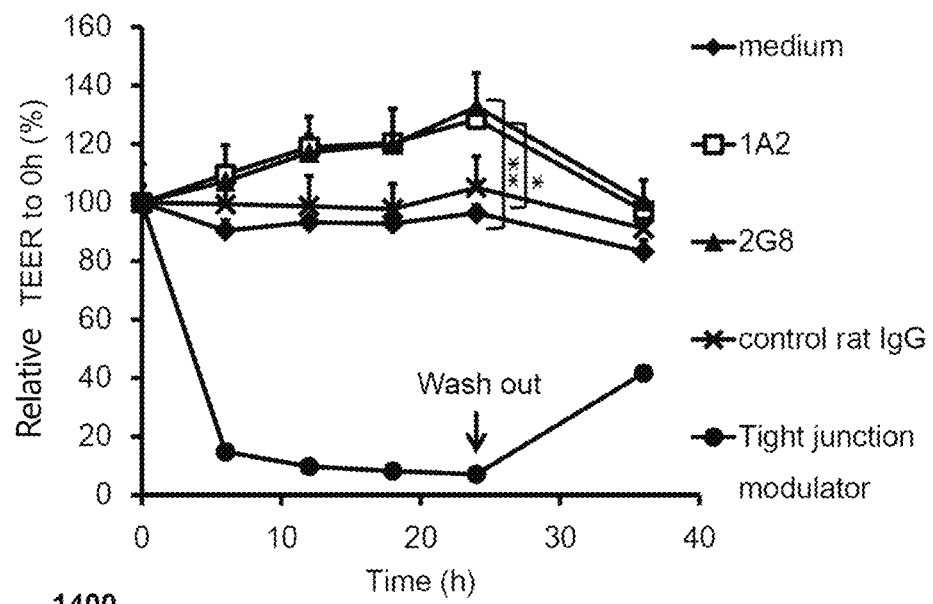
FIG. 8 is a diagram showing the results of TEER measurement performed in Example 9.
Figure 8:
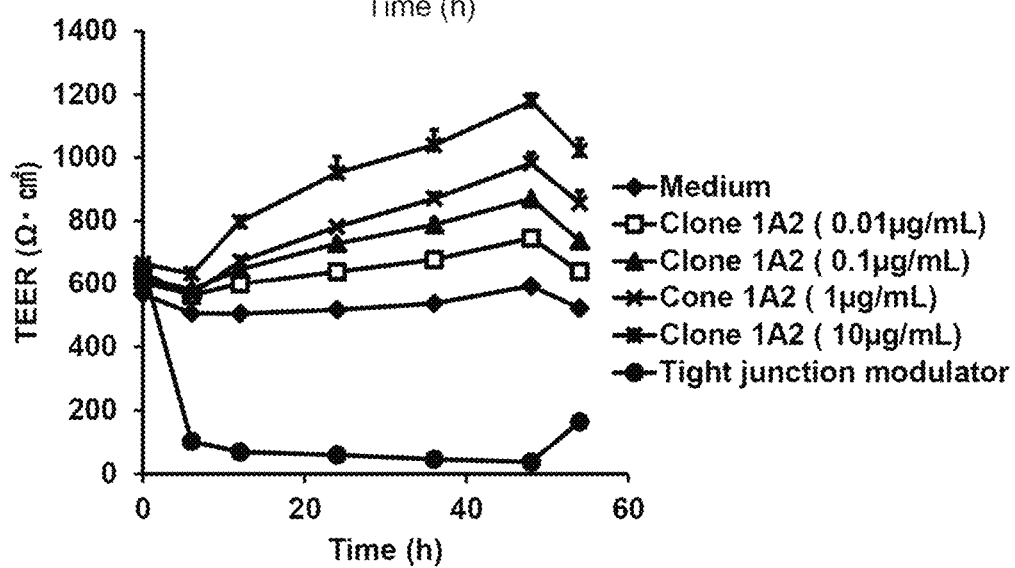

Similarly, 10 days after cell seeding, when the TEER value was stabilized, the medium of pre-cultured cells was removed. 100 μL of medium was added to the top wells, whereas anti-CL-2 antibody solutions prepared by adjusting anti-CL-2 antibody 1A2 to 0.01 μg/mL, 0.1 μg/mL, 1 μg/mL, and 10 μg/mL in medium, a 20 μg/mL TJ modulator, and a medium were individually added in an amount of 600 μL to the bottom wells. Culturing was performed at 37° C. in a 5% $CO_2$ atmosphere. 0, 6, 12, 24, 36, and 48 hours after adding these various solutions, TEER values were measured. The medium of the top wells and the antibody dilution of the bottom wells were then removed and the wells were washed with PBS. 100 μL of medium was newly placed in the top wells, and 600 μL of medium was newly placed in the bottom wells. After 6 hours, TEER values were measured. FIG. 8 B shows the results of TEER measurement.

Figure 9:
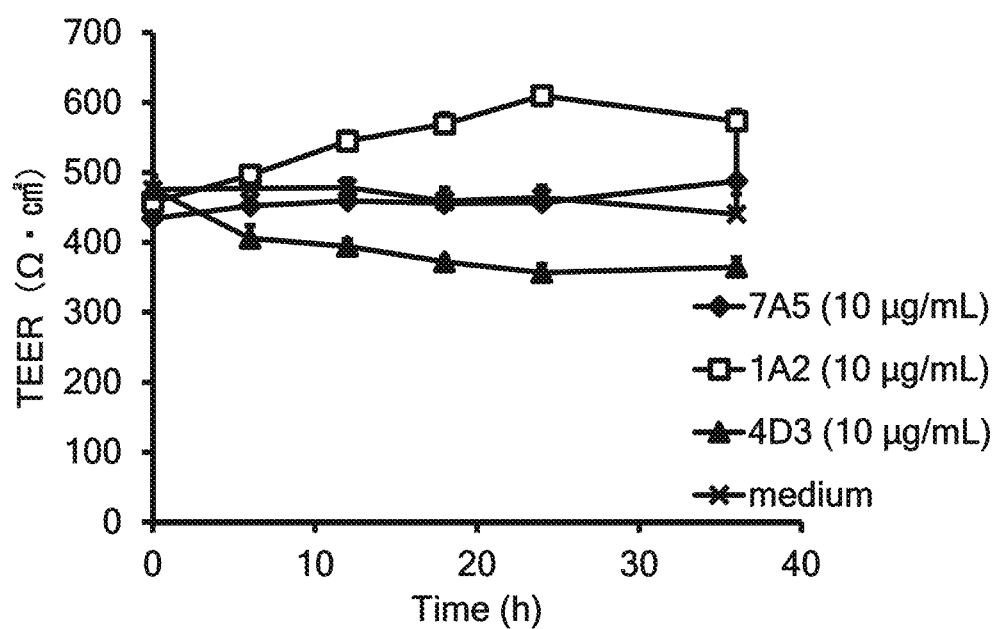
FIG. 9 is a diagram showing the results of TEER measurement performed in Example 9.

Further, similarly, 10 days after seeding cells, when the TEER value was stabilized, the medium of precultured cells was removed. 100 μL of medium was added to the top wells, whereas an anti-CL-1 antibody solution (7A5), an anti-CL-2 antibody solution (1A2), and an anti-CL-4 antibody solution (4D3), each prepared by adjusting the antibody to 10 μg/mL in medium, and a rat IgG antibody solution prepared by adjusting the rat IgG antibody to 10 μg/mL in medium were individually added in an amount of 600 μL to the bottom wells. Culturing was performed at 37° C. in a 5% $CO_2$ atmosphere. 0, 6, 12, 18, and 24 hours after adding these various antibody solutions, TEER values were measured. Subsequently, the medium of the top wells and the antibody dilutions of the bottom wells were removed and the wells were washed with PBS. 100 μL of medium was newly placed into the top wells, and 600 μL of medium was newly placed into the bottom wells. After 12 hours, TEER values were measured. FIG. 9 shows the results of TEER measurement. FIG. 9 shows the ratio of TEER values at various times, based on the TEER value at 0 hour after adding the antibody solutions being defined as 100.

As is apparent from FIG. 8, the anti-CL-2 antibody was found to increase the TEER value in a concentration-dependent manner and enhance TJ-barrier function.

Further, as is apparent from FIG. 9, since the addition of anti-CL-1 antibody does not reduce the TEER value, the anti-CL-1 antibody is considered not to affect TJ barrier function. On the other hand, since the addition of anti CL-4 antibody reduces the TEER value, the results suggest that the anti-CL-4 antibody reduces TJ barrier function. In contrast, as described above, the addition of anti-CL-2 antibody increased the TEER value and was found to enhance TJ-barrier function. The above results show that the anti-CL-2 antibody has a TJ barrier function-enhancing activity.

Example 10: Analysis of Effect of TNF-α on TJ-Barrier Function

Caco-2 cells seeded in a trans-well were cultured in the same manner as in Example 9. Ten days after cell seeding, when the TEER value was stabilized, TNF-α (R&D systems), an inflammatory cytokine, was adjusted to 10 ng/mL in medium, and the medium of pre-cultured cells was removed. 100 μL of the medium was added to the top wells, whereas 600 μL of a TNF-α solution was added to the bottom wells. Culturing was performed at 37° C. in a 5% $CO_2$ atmosphere. 0, 24, and 48 hours after adding TNF-α, TEER values were measured. Further, after 48 hours, the cells were recovered, and western blotting analysis was performed in the same manner as in Example 6.

Figure 10:
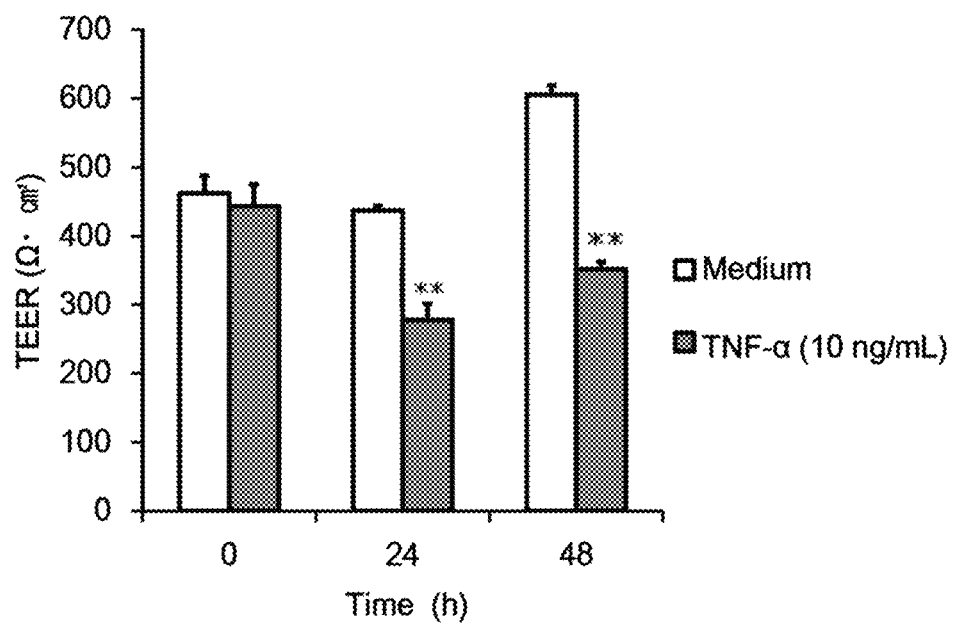
FIG. 10 contains diagrams showing the results of TEER measurement (A) and Western blotting analysis (B) performed in Example 10.
Figure 10:

FIG. 10 shows the TEER values and the results of Western blotting analysis. FIG. 10A shows the results of TEER measurement. FIG. 10 B is a diagram showing the results of Western blotting analysis.

As is apparent from FIG. 10, the addition of TNF-α to Caco-2 cells was confirmed to decrease the TEER value and increase the CL-2 expression level.

Example 11: Analysis of Effect of Anti-CL-2 Antibody on TJ Barrier Function in the Presence of TNF-α

Figure 11:
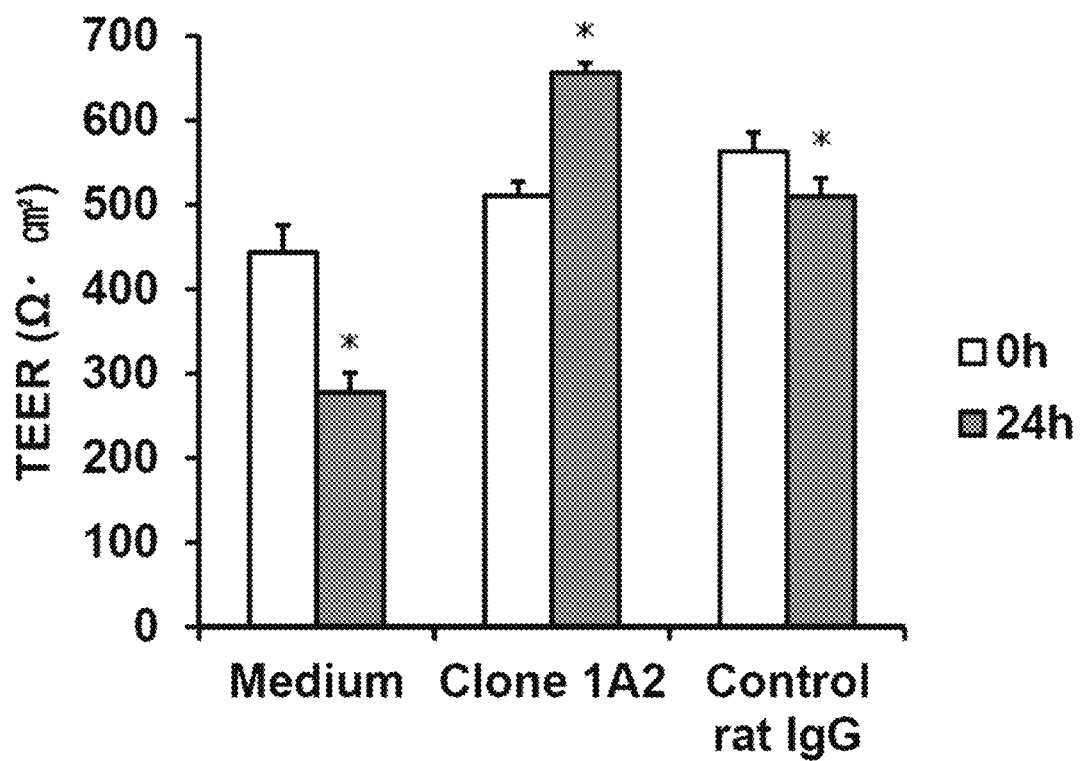
FIG. 11 is a diagram showing the results of TEER measurement performed in Example 11.

Caco-2 cells seeded in trans-wells were cultured in the same manner as in Example 9. Ten days after seeding cells, when the TEER value was stabilized, the medium of pre-cultured cells was removed. 100 μL of medium was added to the top wells, whereas 600 μL of a medium containing TNF-α (10 ng/mL), a medium containing TNF-α (10 ng/mL) and anti-CL-2 antibody 1A2 (10 μg/mL), or a medium containing TNF-α (10 ng/mL) and rat IgG antibody (10 μg/mL) was added to the bottom wells. Culturing was performed at 37° C. in a 5% $CO_2$ atmosphere. Before addition (0 hour) and 24 hours after adding the medium or the like, TEER values were measured. FIG. 11 shows the results of TEER measurement.

Figure 12:
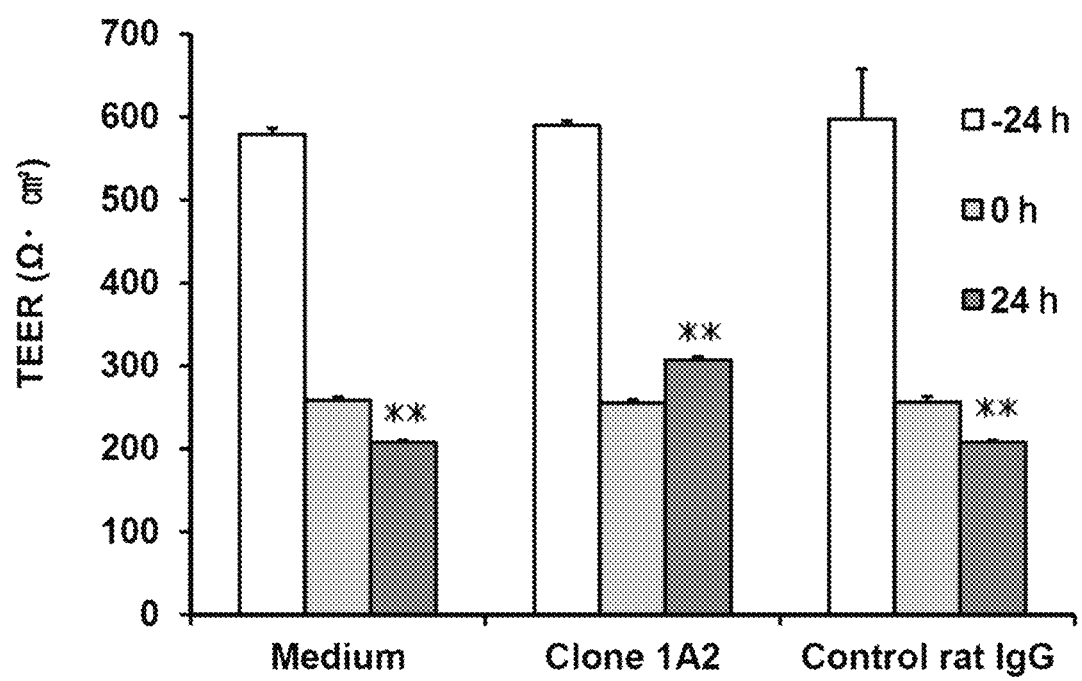
FIG. 12 is a diagram showing the results of TEER measurement performed in Example 11.

Further, Caco-2 cells seeded in trans-wells were cultured in the same manner as in Example 10. Ten days after cell seeding, when the TEER value was stabilized, the medium of the precultured cells was removed. 100 μL of medium was added to the top wells, whereas 600 μL of a TNF-α (10 ng/mL) solution was added to the bottom wells. After culturing was performed at 37° C. in a 5% $CO_2$ atmosphere for 24 hours, TEER values were measured, and the medium was then removed. 100 μL of medium was added to the top wells, whereas 600 μL of a medium containing TNF-α (10 ng/mL), a medium containing TNF-α (10 ng/mL) and anti-CL-2 antibody 1A2 (10 μg/mL), or a medium containing TNF-α (10 ng/mL) and rat IgG antibody (10 μg/mL) was added to the bottom wells. Culturing was performed at 37° C. in a 5% $CO_2$ atmosphere. Before addition (0 h) and 24 hours after adding the medium or the like, TEER values were measured. FIG. 12 shows the results of TEER measurement. In FIG. 12, the time point of adding the medium containing TNF-α solution and anti-CL-2 antibody, or the like is defined as "0 h." Accordingly, "-24 h" indicates the time point of adding the TNF-α solution; and "24 h" indicates 24 hours after adding the medium containing TNF-α solution and anti-CL-2 antibody, or the like.

As is apparent from FIG. 11, the TEER value was confirmed to increase in the anti-CL-2 antibody 1A2-added group, whereas the TEER value decreased in the rat IgG antibody-added group. The results show that the addition of the anti-CL-2 antibody not only can prevent the reduction of TJ barrier function by inflammatory cytokines, such as TNF-α, but also can enhance the TJ barrier function.

Further, as is apparent from FIG. 12, the TEER value reduced by TNF-α treatment was confirmed to increase in the anti-CL-2 antibody 1A2-added group. The results show that the addition of anti-CL-2 antibody can improve the TJ barrier function reduced by inflammatory cytokines, such as TNF-α.

Example 12: Analysis of Effect Combined with Existing Drug

Figure 13:
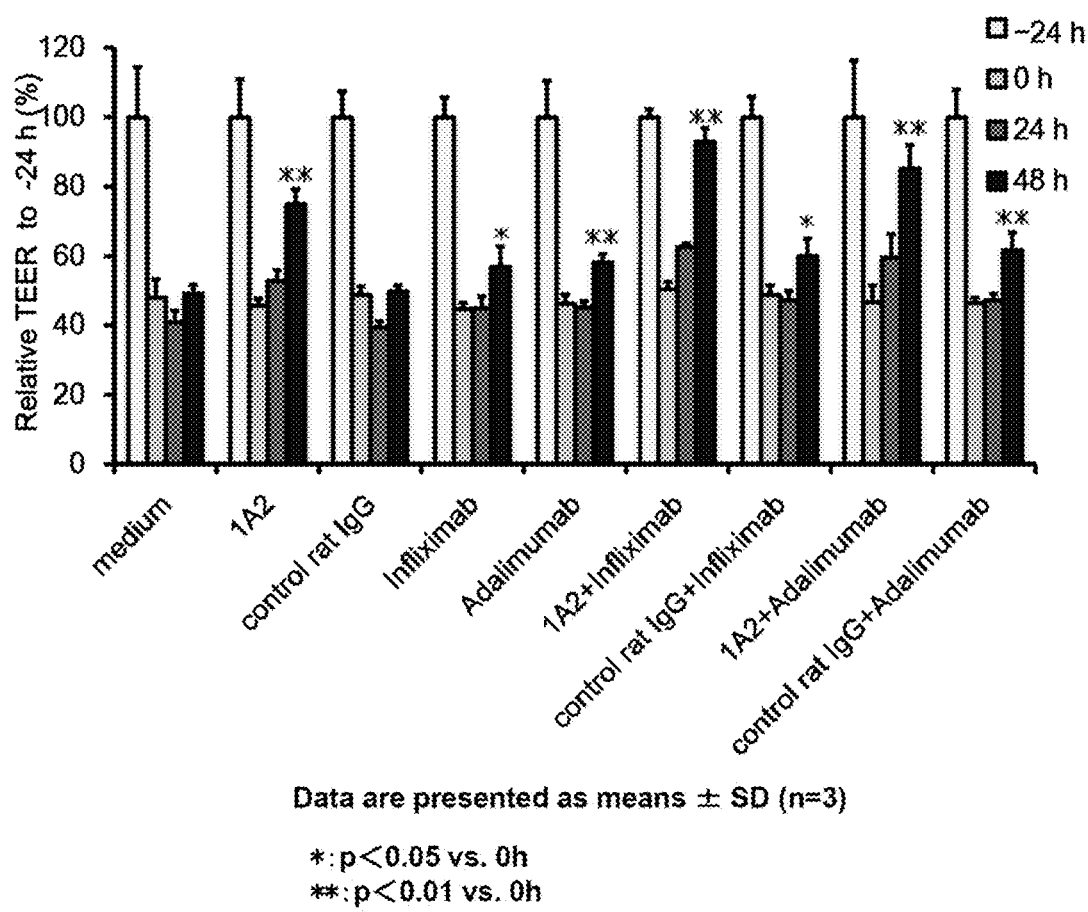
FIG. 13 is a diagram showing the results of TEER measurement performed in Example 12.

Caco-2 cells seeded in trans-wells were cultured in the same manner as in Example 9. Ten days after cell seeding, when the TEER value was stabilized, the medium of pre-cultured cells was removed. 100 μL of medium was added to the top wells, whereas 600 μL of a TNF-α (10 ng/mL) solution was added to the bottom wells. After culturing was performed at 37° C. in a 5% $CO_2$ atmosphere for 24 hours, TEER values were measured, and the medium was then removed. 100 μL of medium was added to the top wells, whereas 600 μL of a mixed solution of TNF-α (10 ng/mL) with each antibody solution described below was added to the bottom wells. After culturing was performed at 37° C. in a 5% $CO_2$ atmosphere for 24 hours and 48 hours, TEER values were measured. The antibody solutions used were an anti-CL-2 antibody 1A2 solution (10 μg/mL), an infliximab (anti-TNF-α antibody) solution (10 μg/mL), an adalimumab (anti-TNF-α antibody) solution (10 μg/mL), a mixed solution of anti-CL-2 antibody 1A2 solution (5 µg/mL) and infliximab solution (5 µg/mL), a mixed solution of rat IgG antibody solution (5 µg/mL) and infliximab solution (5 µg/mL), a mixed solution of anti-CL-2 antibody 1A2 solution (5 µg/mL) and adalimumab solution (5 µg/mL), and a mixed solution of rat IgG antibody solution (5 µg/mL) and adalimumab solution (5 µg/mL). As a control, culturing was performed in the same manner except that 600 µL of a rat IgG-antibody (10 µg/mL) solution was added to the bottom wells. FIG. 13 shows the results of TEER measurement. In FIG. 13, the time point of adding the mixed solution of TNF-α solution and each antibody solution is defined as "0 h." Accordingly, "−24 h" indicates the time point of adding the TNF-α solution, and "24 h" and "48 h" indicate 24 h and 48 h after adding the mixed solution of TNF-α solution and one of various antibody solutions.

As is apparent from FIG. 13, while the TEER value decreased in the rat IgG antibody-added group, an increase in TEER value was confirmed in the anti-CL-2 antibody 1A2-added group and the anti-TNF-α antibody (infliximab or adalimumab)-added group. In the group to which anti-CL-2 antibody and anti-TNF-α antibody (infliximab or adalimumab) were both added, a additive increase in TEER value was observed. The results show that a combination of anti-CL-2 antibody with a known anti-TNF-α antibody can additively improve the TJ barrier function reduced by inflammatory cytokines, such as TNF-α.

Example 13: Examination of Cellular Uptake of Anti-CL-2 Antibody

Figure 14:
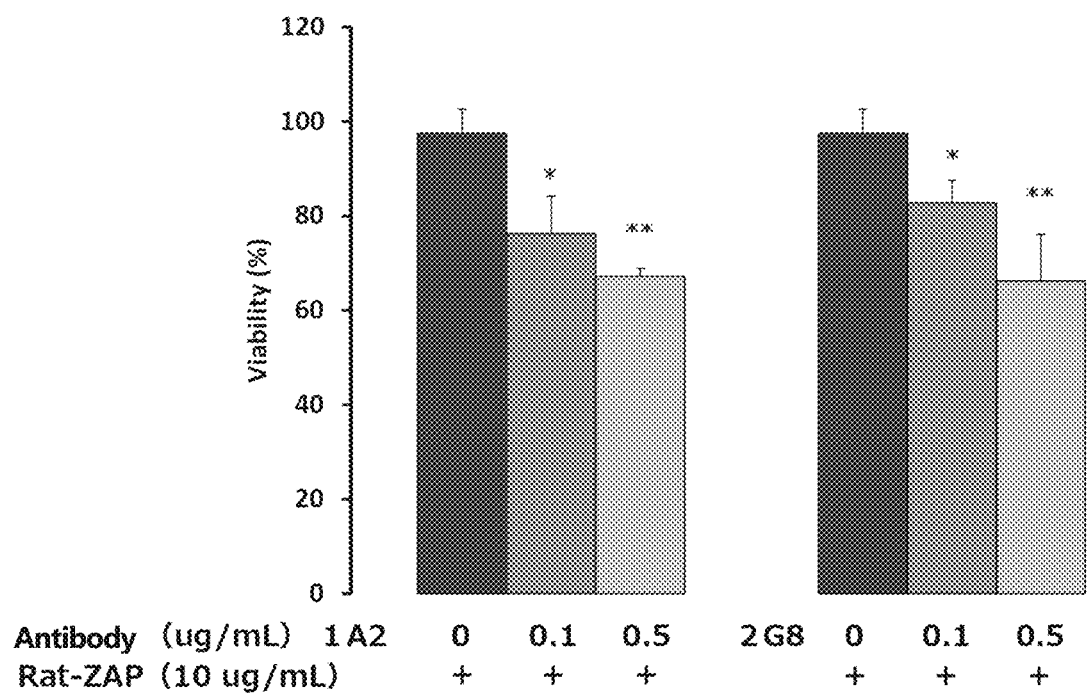
FIG. 14 is a diagram showing the results of cell viability rate calculation performed in Example 13.

T84 cells, which are a human small intestinal epithelial model, were seeded at $2.5 \times 10^5$ cells/well in 96-well plates and cultured overnight, and culture supernatants of the cells were then removed. Antibody solutions prepared by adjusting each of anti-CL-2 antibodies 1A2 and 2G8 to concentrations of 0 (no addition of antibodies), 0.1, and 0.5 µg/mL were individually added in an amount of 100 µL, and culturing was performed for 2 days. After culture supernatants of the cells were removed, the medium was replaced with 90 µL of fresh medium, and 10 µL of a solution of saponin-labeled anti-rat antibody Rat-Zap (Advanced Targeting Systems) adjusted with PBS to a concentration of 10.0 µg/mL was added to the medium. Culturing was performed for 72 hours. Rat-Zap is an antibody that exhibits cytotoxicity when taken up into cells. Rat-Zap is not taken up into cells alone. After 72 hours, 10 µL of WST-8 reagent (Nacalai tesque, Inc.) was added. After culturing at 37° C. for 1 hour, absorbance was measured at 450 nm. The relative absorbance at various antibody concentrations was determined, based on the absorbance of the antibody-free group as a reference. The cell viability rate was calculated. FIG. 14 shows the results.

As is apparent from FIG. 14, the cell viability rate of the anti-CL-2 antibody 1A2-added group and the anti-CL-2 antibody 2G8-added group was confirmed to decrease in a concentration-dependent manner, as compared with the antibody-free group. The results are considered to indicate that the anti-CL-2 antibodies are taken up into cells by binding to CL-2. The results thus suggest that that anti-CL-2 antibody can be used as a carrier for delivering drugs or the like to CL-2 expressing cells.

Example 14: Evaluation of CDC Activity of Anti CL-2 Human-Rat Chimeric Antibody

Figure 15:
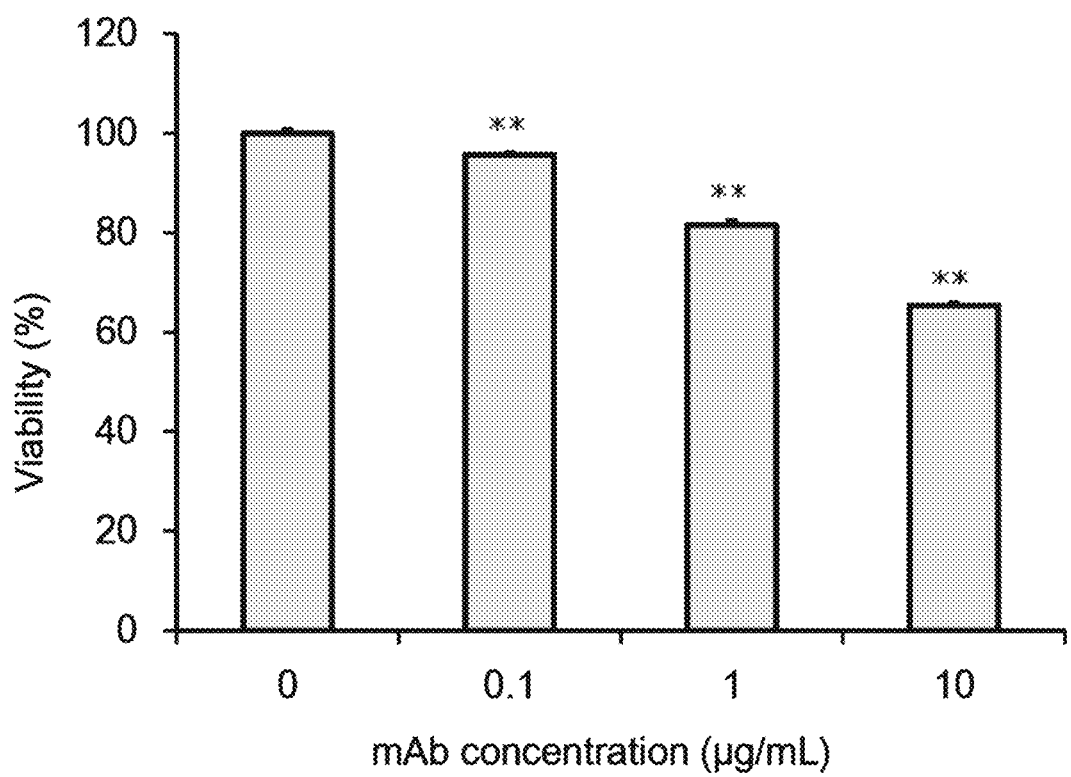
FIG. 15 is a diagram showing the results of cell viability rate calculation performed in Example 14.

90 µL of a suspension of 10% human complement serum (SIGMA) and hCL-2/HT1080 cells ($1.0 \times 10^5$ of cells/well) in Opti-MEM1 Reduced Serum Media (Life Technologies) was seeded, and antibody solutions prepared by adjusting the anti-CL-2 chimeric antibody 1A2 produced in Example 4 to 0 (no addition of antibody), 1, 10, and 100 µg/mL were individually added in an amount of 10 µL. Culturing was performed at 37° C. in a 5% $CO_2$ atmosphere for 3 hours. After 3 hours, 10 µL of WST-8 reagent (Nacalai tesque, Inc.) was added. After culturing was performed at 37° C. for 1 hour, the absorbance was measured at 450 nm. The relative absorbance at various antibody concentrations was determined, based on the absorbance of the antibody-free group as a reference. The cell viability rate was calculated. FIG. 15 shows the results.

As is apparent from FIG. 15, the cell viability rate in the anti CL-2 chimeric antibody-added group was confirmed to decrease in a concentration-dependent manner, as compared with the antibody-free group. The results show that the anti-CL-2 chimeric antibody has complement-dependent cytotoxic activity (CDC-activity).

Figure 16:
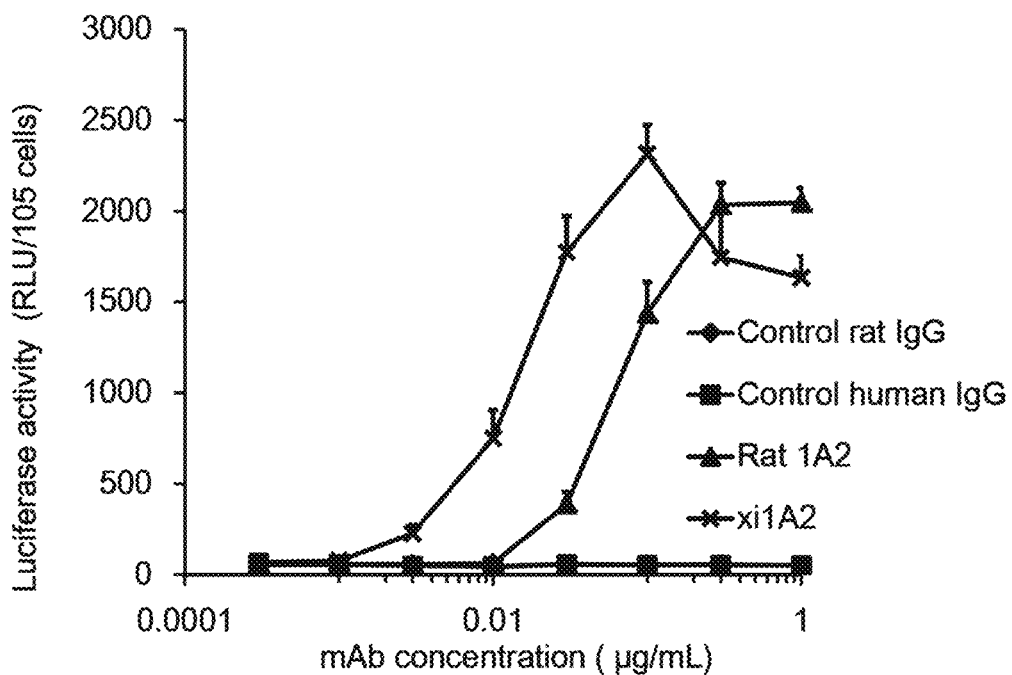
FIG. 16 contains diagrams showing the results of luciferase activity measurements (A and B) performed in Example 15.
Figure 16:
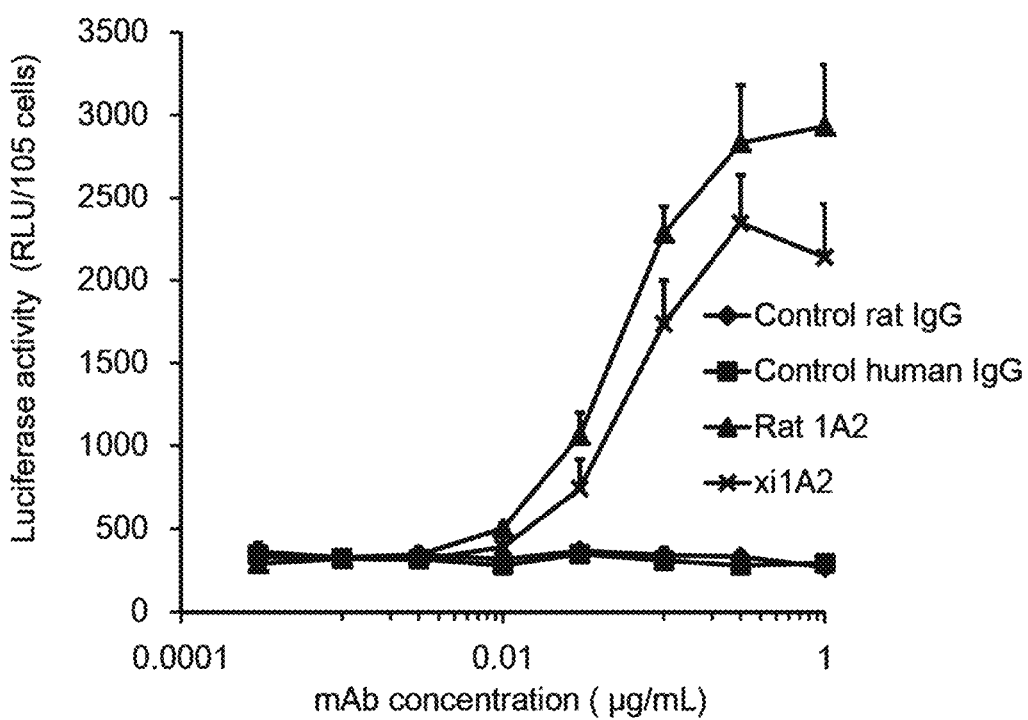

Example 15: Evaluation of Fcγ Receptor Activating Ability of Anti-CL-2 Chimeric Antibody The ability to activate Fcγ receptor, which is one of the indicators of antibody-dependent cytotoxic activity (ADCC activity), was evaluated by the following method. In this example, a cell line in which activation of the Fcγ receptor can be monitored by luciferase expression was used (Tada et al., PLoS One, 9, e95787, 2014).

hCL-2/HT1080 cells ($1 \times 10^4$ cells/well) were seeded in 96-well plates and cultured at 37° C. in a 5% $CO_2$ atmosphere for 1 day, and supernatants were then removed. Suspensions of Jurkat/FcγRIIIa/NFAT-Luc and Jurkat/FcγRIIa/NFAT-Luc in Opti-MEM1Reduced Serum Media were individually seeded at $1 \times 10^5$ cells/well/90 µL. Anti-CL-2 antibody 1A2, anti-CL-2 chimeric antibody 1A2, rat IgG antibody, and human IgG antibody were then individually added in an amount of 10 µL. Co-culture was performed at 37° C. in a 5% $CO_2$ atmosphere for 5 hours. After the culturing, luciferase activity was measured by the ONE-Glo Luciferase Assay System (Promega). FIG. 16 shows the results of luciferase activity measurement. FIG. 16 A shows the measurement results of luciferase activity obtained by using Jurkat/FcγRIIIa/NFAT-Luc. FIG. 16 B shows the measurement results of luciferase activity obtained by using the Jurkat/FcγRIIa/NFAT-Luc.

Figure 17:
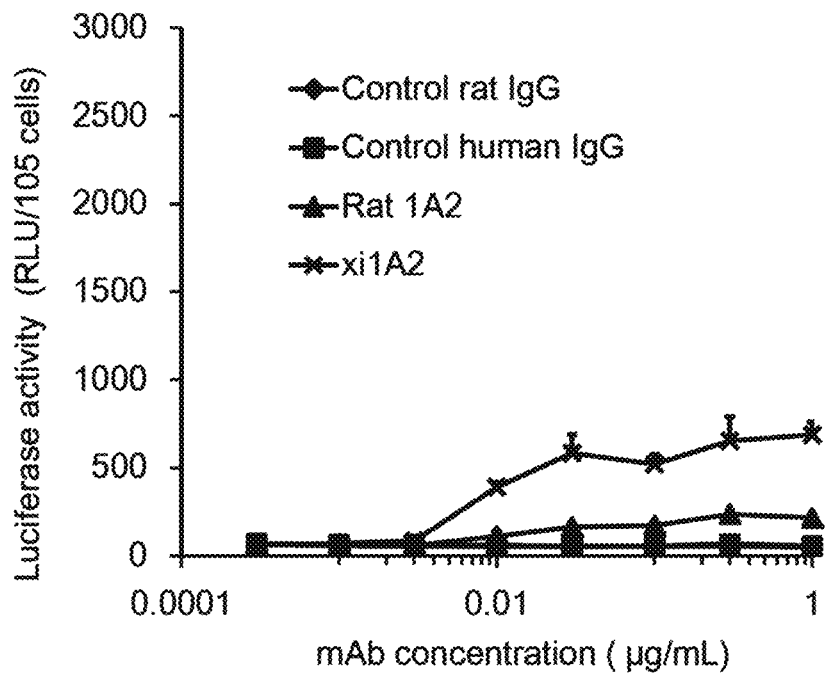
FIG. 17 contains diagrams showing the results of luciferase activity measurements (A and B) performed in Example 15.
Figure 17:
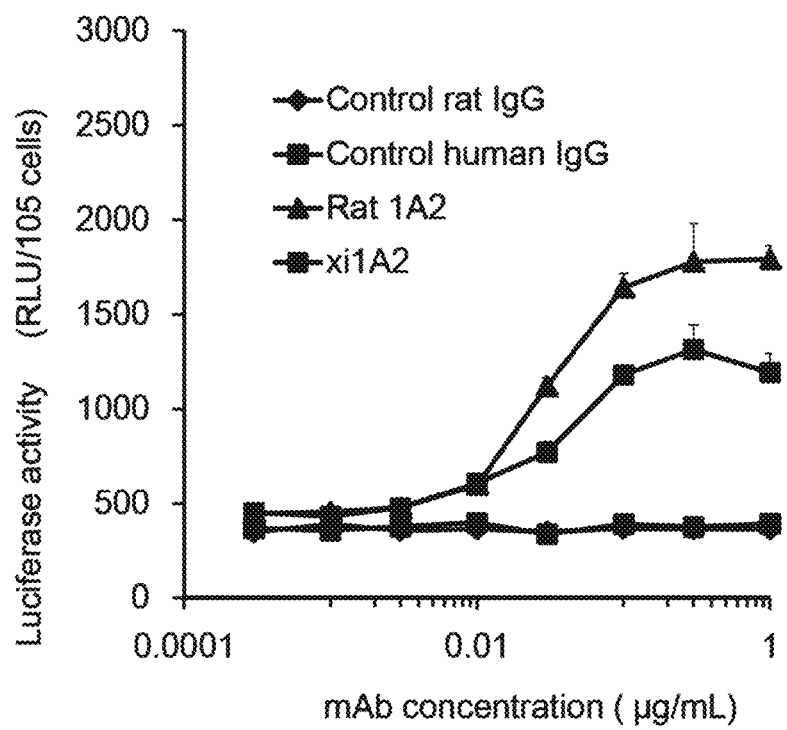

Further, mCL-2/L cells ($1 \times 10^4$ cells/well) were seeded in 96-well plates in the same manner as above and cultured at 37° C. in a 5% $CO_2$ atmosphere for 1 day, and supernatants were then removed. After suspensions of Jurkat/FcγRIIIa/NFAT-Luc and Jurkat/FcγRIIa/NFAT-Luc in Opti-MEM1 Reduced Serum Media were individually seeded at $1 \times 10^5$ cells/well/90 µL, anti-CL-2 antibody 1A2, anti-CL-2 chimeric antibody 1A2, rat IgG antibody, and human IgG antibody were individually added in an amount of 10 µL, and co-culture was performed at 37° C. in a 5% $CO_2$ atmosphere for 5 hours. After the culture, luciferase activity was measured by the ONE-Glo Luciferase Assay System (Promega). FIG. 17 shows the results of luciferase activity measurement. FIG. 17 A shows the measurement results of luciferase activity obtained by using the Jurkat/FcγRIIIa/NFAT-Luc. FIG. 17 B shows the measurement results of luciferase activity obtained by using Jurkat/FcγRIIa/NFAT-Luc.

As is apparent from FIGS. 16 and 17, the anti-CL-2 antibody 1A2 and the anti-CL-2 chimeric antibody 1A2 were both confirmed to activate the FcγIIa receptor and the FcγIIa receptor in a concentration-dependent manner in the presence of hCL-2/HT1080 cells, or in the presence of mCL-2/L cells. The results show that the anti-CL-2 antibody 1A2 and the anti-CL-2 chimeric antibody 1A2 both have the ability to activate NK-cells, neutrophils, macrophages, and the like that express Fcγ receptors in the presence of hCL-2 expressing cells.

Example 16: Evaluation of ADCC Activity of Anti-CL-2 Chimeric Antibody

Figure 18:
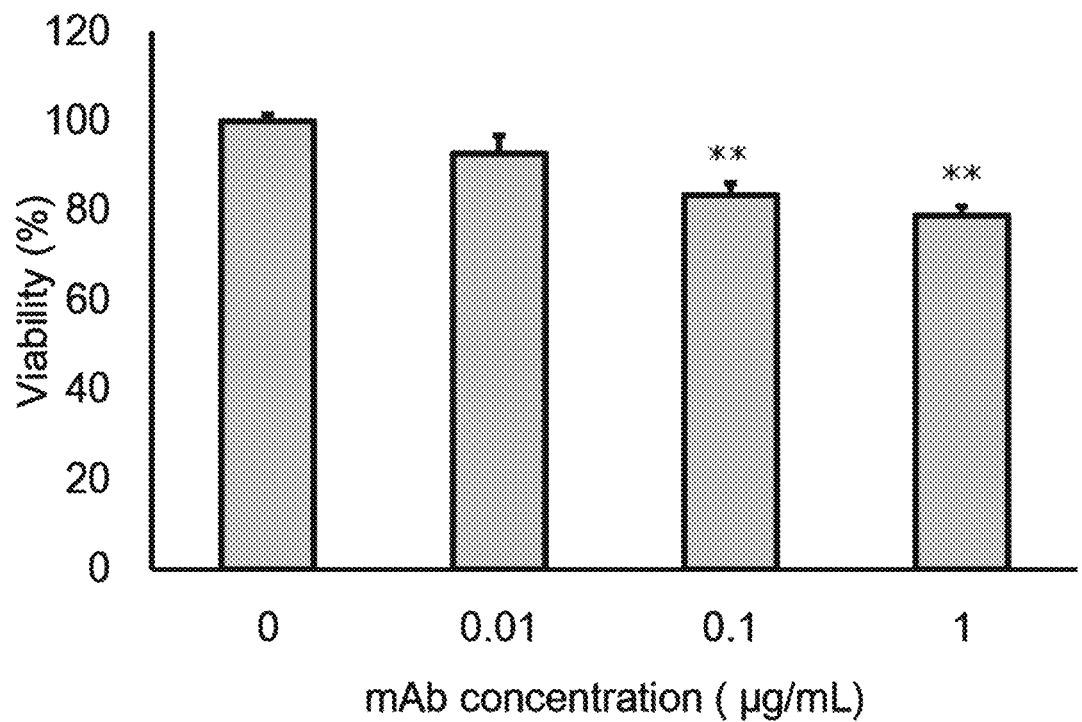
FIG. 18 is a diagram showing the results of cell viability rate calculation performed in Example 16.

Peripheral blood mononuclear cells (PBMC) (Precision Bioservices) were dissolved at 37° C. One vial of PBMC ($10 \times 10^6$ cells) was washed with RPMI1640 and then suspended in RPMI1640. hCL-2/HT1080 cells suspended in RPMI1640 and PBMC were seeded in 96-well plates at $1 \times 10^4$ cells/well/90 µL and $2 \times 10^5$ cells/well/90 µL, respectively. Antibody solutions or culture media each prepared by adjusting anti-CL-2 chimeric antibody 1A2 to final concentrations of 0 (no addition of antibody), 0.01, 0.1, and 1 µg/mL were individually added in an amount of 20 µL. Culturing was performed at 37° C. in a 5% $CO_2$ atmosphere for 4 hours. After 4 hours, 10 µL of WST-8 reagent (Nacalai tesque, Inc.) was added. After culturing was performed at 37° C. for 1 hour, the absorbance was measured at 450 nm. The relative absorbance at various antibody concentrations was determined, based on the absorbance of the antibody-free group as a reference. The cell viability rate was calculated. FIG. 18 shows the results.

As is apparent from FIG. 18, the cell viability rate in the anti-CL-2 chimeric antibody-added group was confirmed to decrease in a concentration-dependent manner, as compared with the antibody-free group. The results showed that the anti-CL-2 chimeric antibody has antibody-dependent cytotoxic activity (ADCC activity).

Example 17: Evaluation of Tumor Accumulation of Anti CL-2 Antibody

Figure 19:
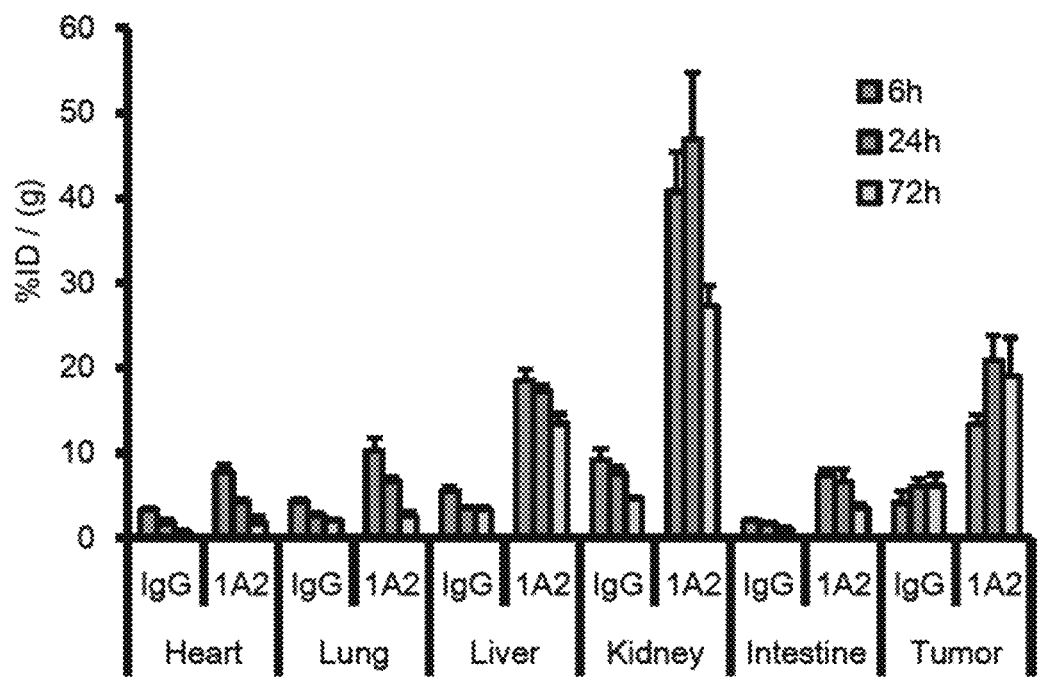
FIG. 19 is a diagram showing the results of fluorescence intensity measurement performed in Example 17.

Fluorescently labeled antibodies in which the lysine residue in constant regions of anti-CL-2 antibody 1A2 and rat IgG antibody was chemically modified with CF750 (a fluorescent material) were prepared in accordance with the protocol of a XenoLight CF fluorescent labeling kit (Caliper). Specifically, 1 mg of each antibody and 0.05 µmol of CF750 were mixed and allowed to react at room temperature for 1 hour. Samples were collected in centrifuge tubes with filters, washed with PBS (pH 7.4) 3 times, then dissolved in 1 ml of PBS, and filtered through a 0.22 µm filter. The protein concentrations were then determined by the absorbance method. The fluorescently labeled antibodies produced by these procedures are hereinafter referred to as "CF750-labeled anti-CL-2 antibody 1A2" and "CF750-labeled rat IgG antibody."

hCL-2/HT1080 cells ($1.0 \times 10^7$ cells/mouse) were subcutaneously administered to BALB/c Slc-nu/nu mice (female, 7 weeks old). After 4 weeks, when the tumor had become sufficiently large, the CF750-labeled anti-CL-2 antibody 1A2 and CF750-labeled rat IgG antibody produced above (20 µg per mouse) were intravenously administered. The fluorescence intensity of the whole image of each mouse was photographed with an imaging device (Maestro EX) 6 hours, 24 hours, and 72 hours after the administration. The heart, lungs, liver, kidneys, intestines, and tumors were then isolated, and their fluorescence intensities were measured with the imaging device described above and analyzed by software (Maestro 2.10.0). The fluorescence intensity of each organ was measured in terms of % injected dose/g (% ID/g). FIG. 19 shows the results.

As is apparent from FIG. 19, the anti-CL-2 antibody 1A2 was accumulated in the tumor tissue 6 hours after the administration. The results show that anti-CL-2 antibody is capable of targeting CL-2 expressing cells in vivo.

Example 18: Evaluation of Antitumor Effect of Anti-CL-2 Antibody hCL-2/HT1080 cells ($1.0 \times 10^7$ cells/mouse) were subcutaneously administered to BALB/c Slc-nu/nu mice (female, 7 weeks old). Control rat IgG (R&D Systems) (1 mg/kg body weight) and anti-CL-2 antibody 1A2 (1 mg/kg body weight) were intraperitoneally administered twice a week for 4 weeks from the date of transplantation. Before each administration, the mice were weighed and tumor size was measured. The tumor size was calculated based on the following formula [1].

$$\text{Tumor volume (mm}^3\text{)} = \text{length} \times \text{width}^2/2 \qquad [1]$$

Figure 20:
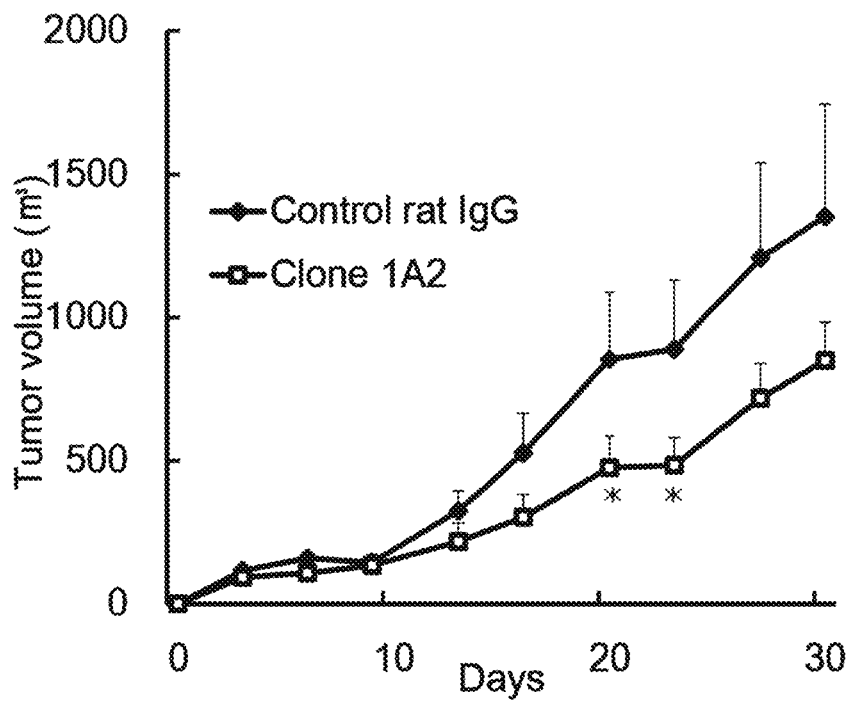
FIG. 20 contains diagrams showing the results of measurements of tumor size (A) and mouse body weight (B) performed in Example 18.
Figure 20:
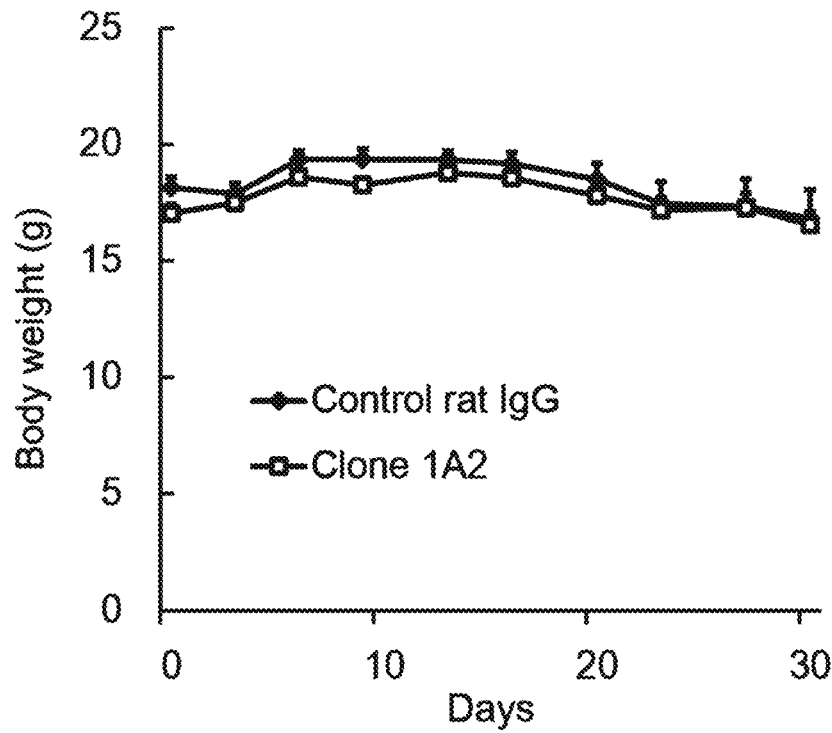

FIG. 20 shows changes in mouse body weight and tumor size from the day of transplantation to 4 weeks after the transplantation.

As is apparent from FIG. 20A, a significant tumor growth inhibitory effect was confirmed in the anti-CL-2 antibody-administered group, as compared with the rat IgG antibody-administered group. Further, as is apparent from FIG. 20B, no side effect of weight loss was confirmed in the anti-CL-2 antibody-administered group.

Example 19: Evaluation of Therapeutic Effect of Anti-CL-2 Antibody on Inflammatory Bowel Disease Claudin-2 is known as a claudin that promotes passive transport of inorganic ions, i.e., that promotes leakage. It is known that the expression of claudin-2 having this characteristic increases in inflammatory bowel diseases and intestinal barrier breakdown occurs therewith. Since the inhibition of TNF-α, which is an inflammatory cytokine, inhibits claudin-2 expression and thus maintains the intestinal barrier, inhibiting claudin-2 to thereby maintain the intestinal barrier is considered to be one of the therapeutic strategies for inflammatory bowel diseases. Accordingly, the therapeutic effect of claudin-2 antibody 1A2 against inflammatory bowel diseases was examined by using a $CD4^+$ $CD45RBh^{high}$T-cell transfer model.

(1) Purification of Spleen CD4+$CD45^{high}$ T cells

Spleens were removed from 8-week-old, male, BALB/c mice (SLCs). Erythrocytes were removed from spleen cells by using an erythrocyte hemolysis buffer. After the addition of 2% NCS-PBS and centrifugation at 400 g for 5 min, purified anti-mouse CD16/32 antibody (BioLegend: clone 93) was allowed to react with the spleen cells at room temperature for 15 minutes. After the addition of 2% NCS-PBS and centrifugation at 400 g for 5 minutes, rat anti-mouse CD4-APC (BioLegend: clone RM4-5) and rat anti-mouse CD45RB-FITC (BD Bioscience: clone 16A) were allowed to react on ice for 30 minutes. After the addition of 2% NCS-PBS and centrifugation at 400 g for 5 minutes, 7-AAD Viability Staining Solution (BioLegend) was allowed to react on ice for 10 minutes. After the addition of 2% NCS-PBS and centrifugation at 400 g for 5 minutes, $CD4^+$ $CD45RB^{high}$ T cells were recovered using FACSAriaII (BD Bioscience).

(2) Production of T cell Transfer Enterocolitis Model

The recovered CD4+ CD45RB$^{high}$ T cells were transplanted into 8-week-old, male, SCID mice (SLCs) by intraperitoneal injection at 4.0×10$^5$ cells/mouse. Control IgG or claudin-2 antibody 1A2 (300 μg per time) was intraperitoneally administered to the transplanted mice 3 times a week, making a total of 24 times. The body weight of each mouse was measured once a week.

(3) Measurement of Colonic Macrophages and Neutrophils

Eight weeks after the transplantation of CD4+ CD45RB$^{high}$ T cells, the large intestine was excised from SCID mice and the intestinal contents were washed with RPMI. The large intestine was placed in 1% EDTA-2%NCS-RPMI and stirred at 37° C. for 15 minutes. The large intestine was then placed in 1 mg/mL collagenase-2% NCS-RPMI and minced, and then stirred at 37° C. for 20 minutes. After the supernatant was collected, the same procedures were performed again. The collected supernatant was centrifuged at 820 g for 20 minutes. Pellets were suspended in 4 mL of 40% Percoll, layered over 4 mL of 75% Percoll, and centrifuged at 820 g for 20 minutes. The cells that accumulated in the interlayer were recovered and purified anti-mouse CD16/32 antibody (BioLegend: clone 93) was allowed to react at room temperature for 15 minutes. After the addition of 2% NCS-PBS and centrifugation at 400 g for 5 minutes, rat anti-mouse CD11b-APC-Cy7 (BioLegend: clone M1/70), rat anti-mouse Ly6G-FITC (BioLegend: clone 1A8), and rat anti-mouse F4/80-Pacific Blue (BioLegend: clone BM8) were allowed to react on ice for 30 minutes. After the addition of 2% NCS-PBS and centrifugation at 400 g for 5 minutes, 7-AAD Viability Staining Solution (BioLegend) was allowed to react on ice for 10 minutes. After the addition of 2% NCS-PBS and centrifugation at 400 g for 5 minutes, macrophages and neutrophils were measured using FACSAriaII (BD Bioscience).

(4) Fluorescent Immunostaining of Large Intestine Tissue

Eight weeks after CD4+ CD45RB$^{high}$ T cell transplantation, the large intestine was excised from SCID mice. The intestinal contents were washed with RPMI. The large intestine was embedded in an Optimal Cutting Temperature compound (Sakura Finetek) and frozen in liquid nitrogen, and 6 μm sections were then prepared using a cryostat. The sections were fixed by treatment with 99.5% ethanol for 30 minutes and then with 100% acetone for 1 minute. After washing with PBS for 5 minutes twice, 2% NCS-PBS was added, and a reaction was allowed to proceed at room temperature for 30 minutes. After washing with PBS for 5 minutes twice, rabbit anti-claudin-2 (Abcam plc.) was added, and a reaction was allowed to proceed at 4° C. overnight. After washing with PBS for 5 minutes twice, rat anti-mouse CD11b-APC (BioLegend: clone M1/70), rat anti-mouse Ly6G-FITC (BioLegend: clone 1A8), and anti-rabbit Cy3 were added and allowed to react at room temperature for 30 minutes. After washing with PBS for 5 minutes twice, one drop of Fluoro-KEEPER Antifade Reagent (Nacalai tesque, Inc.) was added dropwise, and the sections were mounted therewith.

(5) Hematoxylin-Eosin (HE) Stain of Large Intestine Tissue

Eight weeks after CD4+ CD45RB$^{high}$ T cell transplantation, the large intestine was excised from SCID mice, and the intestinal contents were washed with RPMI. The large intestine was embedded in an Optimal Cutting Temperature compound (Sakura Finetek) and frozen in liquid nitrogen. 6-μm sections were then prepared using a cryostat. The sections were fixed by treatment with 99.5% ethanol for 30 minutes and then with 100% acetone for 1 minute. After washing with running water for 10 minutes, hematoxylin was allowed to react at room temperature for 10 minutes. After washing with running water for 30 minutes, eosin was allowed to react at room temperature for 1 minute. The sections were then immersed in 70% ethanol, 80% ethanol, and 90% ethanol for 10 seconds, 15 seconds, and 20 seconds, respectively, and immersed in 99.5% ethanol for 1 minute twice. The sections were then immersed in xylene for 1 minute 3 times. One drop of Permount Fisher (Fisher Scientific) was added dropwise and the sections were mounted therewith.

(6) Results

Figure 21A:
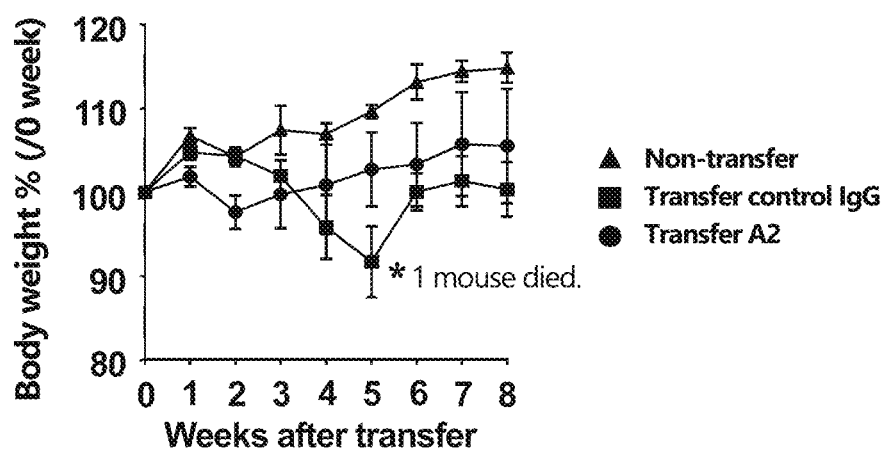
FIG. 21 contains diagrams showing the results of measurements of therapeutic effects against inflammatory bowel disease performed in Example 19.
Figure 21B:
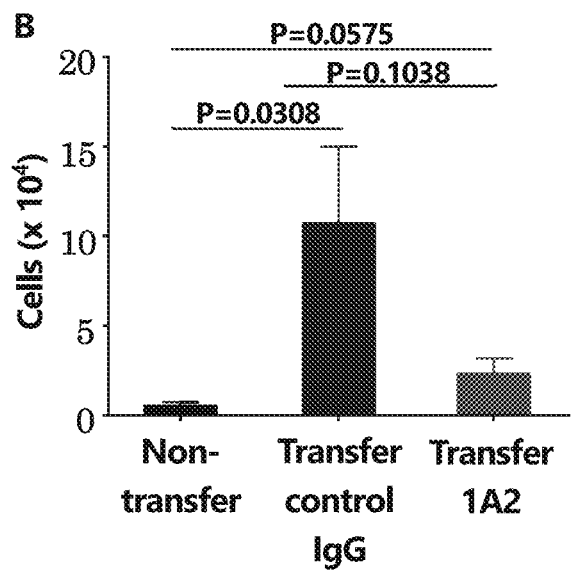
Figure 21C:
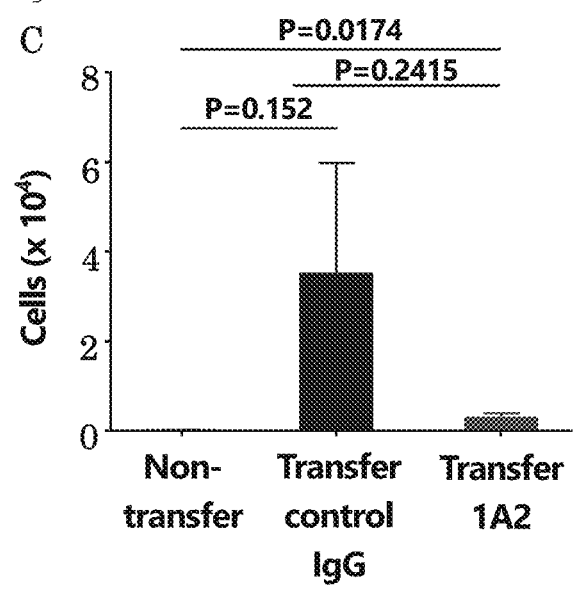
Figure 21D:
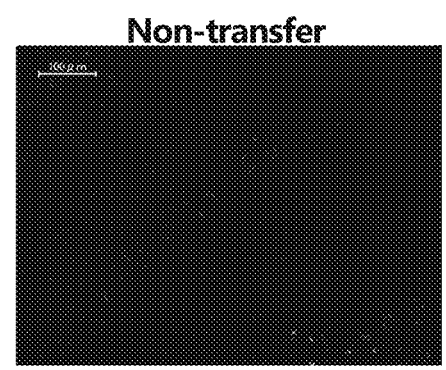
Figure 1:
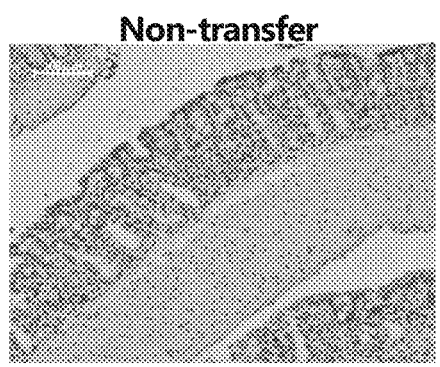
Figure 21D:
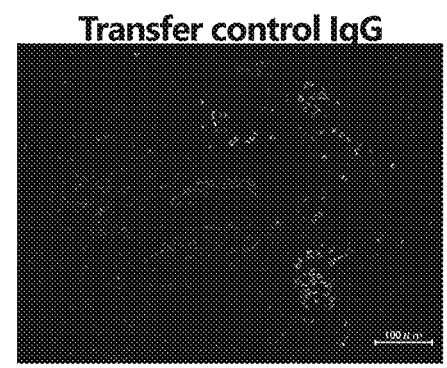
Figure 2:
Figure 21D:
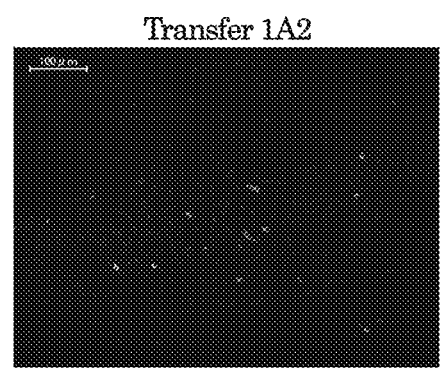
Figure 3:
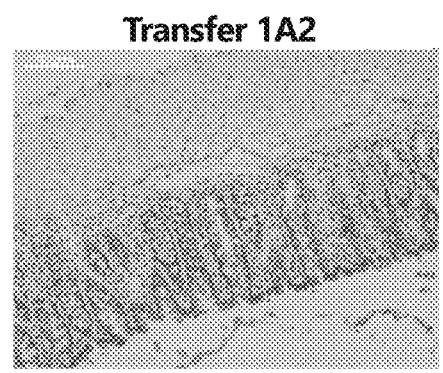

As compared with the control IgG-administered group (in which one mouse died at 5 weeks), the claudin-2 antibody 1A2-administered group was observed to tend to inhibit macrophages and neutrophils, which relate to weight loss and exacerbation of inflammatory bowel diseases (FIG. 21A to 21C). Similarly, histological analysis also showed that infiltration of neutrophils into the mucosal lamina propria was inhibited in the claudin-2 antibody 1A2-administered group (FIG. 21D). Further, administration of claudin-2 antibody 1A2 was also observed to inhibit claudin-2 expression (FIG. 21D). From these results as well as the results of the other examples described above, it can be concluded that claudin-2 antibody 1A2 inhibits tight junction formation of claudin-2 and suppresses intestinal barrier breakdown, and thus has therapeutic effects against inflammatory bowel diseases.

The invention claimed is:

1. A monoclonal antibody that specifically binds to an extracellular region of Claudin-2, the monoclonal antibody comprising:
the heavy-chain variable region comprising the amino acid sequence having at least 90% identity with the amino acid sequence of SEQ ID NO: 13 and the light-chain variable region comprising the amino acid sequence having at least 90% identity with the amino acid sequence of SEQ ID NO: 15;
and wherein the heavy-chain variable region comprising: heavy-chain CDR1 comprising the amino acid sequence of SEQ ID NO: 1, heavy-chain CDR2 comprising the amino acid sequence of SEQ ID NO: 3, and heavy-chain CDR3 comprising the amino acid sequence of SEQ ID NO: 5; and wherein the light-chain variable region comprising: light-chain CDR1 comprising the amino acid sequence of SEQ ID NO: 7, light-chain CDR2 comprising the amino acid sequence of SEQ ID NO: 9, and light-chain CDR3 comprising the amino acid sequence of SEQ ID NO: 11.

2. The monoclonal antibody according to claim 1, wherein the monoclonal antibody recognizes a three-dimensional structure of the extracellular region of Claudin-2.

3. The monoclonal antibody according to claim 1, wherein the extracellular region is an extracellular region first loop of Claudin-2.

4. The monoclonal antibody according to claim 1, wherein the monoclonal antibody has a structure of Fab, Fab', (Fab')$_2$, Fv, scFv, or a combination thereof.

5. The monoclonal antibody according to claim 1, wherein the monoclonal antibody is a chimeric antibody or a humanized antibody.

6. A pharmaceutical composition comprising the monoclonal antibody according to claim 1.

7. The pharmaceutical composition according to claim 6, wherein the pharmaceutical composition is used for the treatment of inflammatory bowel disease.

8. The pharmaceutical composition according to claim 6, wherein the pharmaceutical composition is used for the treatment of cancer.

9. A monoclonal antibody that specifically binds to an extracellular region of Claudin-2, the monoclonal antibody comprising:
the heavy-chain variable region comprising the amino acid sequence having at least 90% identity with the amino acid sequence of SEQ ID NO: 14 and the light-chain variable region comprising the amino acid sequence having at least 90% identity with the amino acid sequence of SEQ ID NO: 16; and wherein the heavy-chain variable region comprising: heavy-chain CDR1 comprising the amino acid sequence of SEQ ID NO: 2, heavy-chain CDR2 comprising the amino acid sequence of SEQ ID NO: 4, and heavy-chain CDR3 comprising the amino acid sequence of SEQ ID NO: 6; and wherein the light-chain variable region comprising: light-chain CDR1 comprising the amino acid sequence of SEQ ID NO: 8, light-chain CDR2 comprising the amino acid sequence of SEQ ID NO: 10, and light-chain CDR3 comprising the amino acid of SEQ ID NO: 12.

10. The monoclonal antibody according to claim 9, wherein the monoclonal antibody recognizes a three-dimensional structure of the extracellular region of Claudin-2.

11. The monoclonal antibody according to claim 9, wherein the extracellular region is an extracellular region first loop of Claudin-2.

12. The monoclonal antibody according to claim 9, wherein the monoclonal antibody has a structure of Fab, Fab', (Fab')$_2$, Fv, scFv, or a combination thereof.

13. The monoclonal antibody according to claim 9, wherein the monoclonal antibody is a chimeric antibody or a humanized antibody.

14. A pharmaceutical composition comprising the monoclonal antibody according to claim 9.

15. The pharmaceutical composition according to claim 14, wherein the pharmaceutical composition is used for the treatment of inflammatory bowel disease.

16. The pharmaceutical composition according to claim 14, wherein the pharmaceutical composition is used for the treatment of cancer.

* * * * *

UNITED STATES PATENT AND TRADEMARK OFFICE
CERTIFICATE OF CORRECTION

PATENT NO. : 11,078,271 B2  
APPLICATION NO. : 16/473413  
DATED : August 3, 2021  
INVENTOR(S) : Kondoh et al.

Page 1 of 1

It is certified that error appears in the above-identified patent and that said Letters Patent is hereby corrected as shown below:

On the Title Page

Item (71), please delete "JAPAN AS REPRESENTED BY DIRECTOR GENERAL OF NATIONAL INSTITUTE OF HEALTH SCIENCES, Kawasaki (JP)".

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*